(12) United States Patent
Chrisope

(10) Patent No.: US 6,468,526 B2
(45) Date of Patent: *Oct. 22, 2002

(54) VAGINAL *LACTOBACILLUS* MEDICANT

(75) Inventor: Gerald L. Chrisope, Boulder, CO (US)

(73) Assignee: GyneLogix, Inc., Louisville, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 10/027,472

(22) Filed: Dec. 21, 2001

(65) Prior Publication Data

US 2002/0090365 A1 Jul. 11, 2002

Related U.S. Application Data

(63) Continuation of application No. 09/478,185, filed on Jan. 5, 2000, now Pat. No. 6,372,209, which is a continuation of application No. 08/834,649, filed on Apr. 11, 1997, now Pat. No. 6,093,394.

(51) Int. Cl.$^7$ .......................... A01N 63/00; C12N 1/00; C12N 1/12; C12N 1/20
(52) U.S. Cl. ................ 424/93.45; 435/243; 435/252.1; 435/252.9
(58) Field of Search ................ 424/93.45; 435/243, 435/252.1, 252.9

(56) References Cited

U.S. PATENT DOCUMENTS

| | | | |
|---|---|---|---|
| 3,639,566 A | 2/1972 | Naito et al. | 424/37 |
| 4,314,995 A | 2/1982 | Hata et al. | 424/93 |
| 4,592,748 A | 6/1986 | Jost | 604/279 |
| 4,689,226 A | 8/1987 | Nurmi et al. | 424/801 |
| 4,765,978 A | 8/1988 | Abidi et al. | 424/80 |
| 4,839,281 A | 6/1989 | Gorbach et al. | 435/34 |
| 4,946,791 A | 8/1990 | Manfredi et al. | 435/257.9 |
| 4,956,177 A | 9/1990 | King et al. | 424/93 |
| 4,980,164 A | 12/1990 | Manfredi et al. | 424/93 |
| 5,032,399 A | 7/1991 | Gorbach et al. | 424/93 |
| 5,176,911 A | 1/1993 | Tosi et al. | 424/93 |
| 5,256,425 A | 10/1993 | Herman et al. | 424/93 |
| 5,296,221 A | 3/1994 | Mitsuoka et al. | 424/93 |
| 5,466,463 A | 11/1995 | Ford | 424/433 |
| 5,573,765 A | 11/1996 | Reinhard et al. | 424/93.45 |
| 5,645,830 A | 7/1997 | Reid et al. | 424/93.45 |
| 5,705,160 A | 1/1998 | Bruce et al. | 424/195.1 |
| 6,093,394 A * | 7/2000 | Chrisope | 424/93.45 |
| 6,277,370 B1 | 8/2001 | Cavaliere Ved. Veseley et al. | 424/93.45 |
| 6,372,209 B1 * | 4/2002 | Chrisope | 424/93.45 |

FOREIGN PATENT DOCUMENTS

| CA | 1298556 | 4/1992 |
| WO | WO 84/04675 | 12/1984 |
| WO | WO 93/09793 | 5/1993 |

OTHER PUBLICATIONS

*The American Heritage Dictionary*, Definition of Trademark.
Hillier, Association between bacterial vaginosis and preterm delivery of a low–birth weight infant, *N. Engl. J. Med.* 333:1737–42 (1995).
Bacterial vaginosis alert, *Child*, 79, Apr. 1995.
CDC update [AIDS News] Does loss of vaginal flora increase risk of STD? *AIDS Alert* 13(7):79 (1998).
Cohen et al., *AIDS*, 1093 (1995).

(List continued on next page.)

*Primary Examiner*—Hankel T. Park
*Assistant Examiner*—Stacy S. Brown
(74) *Attorney, Agent, or Firm*—Sheridan Ross P.C.

(57) ABSTRACT

Disclosed are novel isolated strains of bacteria of the genus Lactobacillus which are useful in a vaginal medicant. Also disclosed are medicants containing such Lactobacilli, a novel preservation matrix for microorganisms, a method for preserving microbial cells within a medicant, and methods for preventing and treating vaginal and gastrointestinal infections.

23 Claims, 8 Drawing Sheets

ELEVATED TEMPERATURE STORAGE OF LACTOBACILLUS STRAIN CTV-05

OTHER PUBLICATIONS

Deneke et al., (1983), *Infection & Immunity*, 39(3):1102–1106.
Eschenbach, *Obstet. Gynecol. Clin. NA* 16:593–610 (1989).
Fitzsimmons et al., *Microbios* 80:125–133 (1994).
Forbes, *HIV Plus* 2::20–26 (1998).
Fuller, (1978), *J. of Applied Bacteriology*, 45:389–395.
Fuller, (1979), *Biological Abstracts*, 67(9), No. 54781.
Gilliland et al., (1977), *J. of Food Protection*, 40(11):760–762.
Gilliland et al., (1978), *Biological Abstracts*, 65(6), No. 34231.
Gravett et al., *JAMA* 256:1899–1903 (1986).
Gravett et al., *Obstet. Gynecol.* 67:229–237 (1986).
Gray et al., Depleted Vaginal Lactobacilli and BV Increase HIV Acquisition in Studies in Uganda and Malawi, Johns Hopkins Univ., Medical Institutions, Baltimore MD; Columbia University, School of Public Health, New York, NY; Makerere University, Kampala, Uganda; University of Pittsburgh, Pittsburgh PA (1997) Lancet, 350: 546–550.
Hashemi et al., Induction of Human Immunodeficiency Virus Type 1 Expression by Anaerobes Associated with Bacterial Vaginosis, The Journal of Infectious Diseases, 2000, 181:1574–80.
Hauth et al., *N. Engl. J. Med.* 333:1732 (1995).
Hawes et al., *JID* 174:1058 (1996), pp. 1058–1063.
Hawrylyshyn et al., *Am. J. Obstet Gynecol.* 139:294–298 (1981).
Hillier et al., *N. Engl. J. Med.* 319:972–988 (1988).
Hillier et al., *Obstet. Gynecol.* 79:369–373 (1992).
Hillier et al., *Clin. Infect. Dis.* 16(suppl. 4):S273 (1993).
Hillier et al., *Clin. Infect. Dis.* 20(suppl 2):S276–278 (1995).
Hillier et al., *AIDS Research & Human Retroviruses* 14(suppl 1):51–55 (1998).
Hillier, Vaginal lactobacilli as natural microbicides. Presentation in Divisional Group II symposium: New Developments in Sexually Transmitted Diseases. American Society for Microbiology Annual Meeting, Atlanta, Georgia (1998).
Hilton et al., *Ann. Intern. Med.* 116:353–357 (1992).
Joesoef et al., Bacterial vaginosis: review of treatment options and potential clinical indications for therapy, Clinical Infectious Diseases 28 (Suppl 1):S57–S65 (1999).
Klebanoff, *J. Bact.,* 95(6):2131–2138 (1968).
Klebanoff et al., *J. Exp. Med.* 174:289–92 (1991).
Krohn et al., *JID*, 171:1475 (1995), pp. 1475–1480.
Larsson et al., *Obstet. Gynecol.* 77:450–453 (1991).
Lomborg, *Child* :4/95:79 (1995).
Marrie et al., *J. Clin. Microbiol.* 8:67–72 (1976).
Martin et al., Journal of Infectious Diseases, 1999, vol. 180, pp. 1863–1868.
Mäyrä–Mäkinen et al., (1983), *J. of Applied Bacteriology,* 55:241–245.
Newton et al., *Obstet. Gynecol.* 75:402–406 (1990).
Paavonen et al., *Br. J. Obstet. Gynecol.* 94:454–460 (1987).
Redondo–Lopez et al., *Rev. Infect. Dis.* 12:856–72 (1990).
Reid et al., (1990) ,*Clinical Micro. Reviews*, 3(4):335–344.
Saigh et al., *Infection & Immunity* 19:704–710 (1978).
Seaward et al., *Am. J. Obstet. Gynecol.* 179:635–9 (1998).
Sewankambo et al., *Lancet* 350:546–50 (1997).
Silva, et al., (1988), Tufts Univ. Sch. of Med., Boston, MA, pp. 1–13.
Silva de Ruiz et al., *Biol. Pharmaceutical Bull* 19:88–93 (1996).
Silver et al., *Am. J. Obstet. Gynecol.* 161:808–812 (1989).
Soper et al., *Am. J. Obstet. Gynecol.* 163:1016 (1990), pp. 1016–1022.
Stone et al., *AIDS*, 8(suppl 1):5285–5293 (1994).
Taha et al., *AIDS* 12:1699 (1998).
Velraeds et al., *Applied and Env. Microbiol.* 62:1958–63 (1996).
Watts et al., *Obstet. Gynecol.* 75:52–58 (1990).
Watts et al., *Obstet. Gynecol.* 79:351–357 (1992).
Wood, et al., (1985), *Am. J. Obstet. Bynecol.,* 153:740–3.

* cited by examiner

FIG. 1 ELEVATED TEMPERATURE STORAGE OF LACTOBACILLUS STRAIN CTV-05

FIG. 2 STORAGE STABILITY OF LACTOBACILLUS STRAIN CTV-05

VAGINAL *LACTOBACILLUS* MEDICANT

RELATED APPLICATIONS

This is a Continuation application of pending prior application Ser. No. 09/478,185, filed Jan. 5, 2000, now Pat. No. 6,372,209, which is a continuation of Ser. No. 08/834,649 filed Apr. 11, 1997 now Pat. No. 6,093,394. The entire disclosure of the prior applications is considered to be part of the disclosure of the accompanying application and are hereby incorporated by reference.

REFERENCE TO GOVERNMENT SUPPORT

This invention was made in part with government support under AI 31448 and R43 AI 36021-01, both awarded by the National Institutes of Health, and CDC 200-94-0819, awarded by the Center for Disease Control. The government has certain rights to this invention.

FIELD OF THE INVENTION

The present invention relates to a bacterium of the genus Lactobacillus with desirable characteristics suitable for use in a vaginal medicant. More particularly, this invention relates to a vaginal medicant having a substantially pure culture of preserved microbial cells, to a preservation matrix, to a method for preserving the microbial cells within the preservation matrix, and to methods for preventing and treating vaginal infections.

BACKGROUND OF THE INVENTION

Lower genital tract infections, including sexually transmitted diseases (STDs) are some of the most common clinical problems among women of childbearing age. Over 10 million office visits each year in the United States are attributed to vaginal complaints. Vaginal discharge can be due to vaginal infections (yeast, bacterial vaginosis and trichomonas) or cervical infections (gonorrhea or chlamydia). Additionally, there is a body of evidence linking vaginal infections to preterm delivery, low birth weight, and neonatal mortality, which are some of the most important problems faced in obstetrics. Bacterial vaginosis is one of the most common genital infections in pregnancy. Women with bacterial vaginosis diagnosed during the second trimester of pregnancy are 40 percent more likely to give birth to a premature, low-birth weight infant than women without bacterial vaginosis. The prevention of even a small proportion of such births could translate into large monetary savings and a decrease in neonatal morbidity and mortality.

Lactobacilli are gram positive rods that are a part of the microbial flora of the human gut, mouth, and vagina. Vaginal Lactobacilli are thought to play an important role in resistance to infection via production of lactic acid and acidification of the vagina or by production of other antimicrobial products, such as hydrogen peroxide $H_2O_2$. It has been demonstrated that women with predominant vaginal Lactobacillus flora have a 50% lower frequency of gonorrhea, chlamydial infections, trichomoniasis and bacterial vaginosis. The presence of $H_2O_2$-producing Lactobacilli in the vagina have been linked to a decreased frequency of bacterial vaginosis, symptomatic yeast vaginitis and sexually transmitted pathogens including *Neisseria gonorrhea, Chlamydia trachomatis,* and *Trichomonas vaginalis.* In vitro studies have demonstrated that $H_2O_2$-producing Lactobacilli have potent bactericidal and viricidal properties against vaginal pathogens and even against human immunodeficiency virus (HIV).

Unfortunately, many women of childbearing age lack vaginal Lactobacilli. The vaginal ecosystem is dynamically affected by medications, general health status, sexual practices and contraception. Many vaginal and systemic medications may kill vaginal Lactobacilli. Hence, treatment of sexually transmitted diseases with antibiotics may place women at increased risk for repeated acquisition of the diseases. These findings, along with the widespread belief that Lactobacilli generally promote vaginal health, have suggested to clinicians that women should recolonize the vagina with Lactobacillus to prevent or treat genital tract infections.

Lactobacillus products for intravaginal or oral use have been available for over 100 years in the form of "acidophilus" preparations available in health food stores, and acidophilus milk or yogurt bought in grocery stores (e.g., these products typically advertise the inclusion of a strain of *Lactobacillus acidophilus*). These products have included vaginal suppositories containing lyophilized *Lactobacillus acidophilus* of human origin as well as various nutritional supplements. These products have been largely non-efficacious due to the failure of the products to colonize the vagina with the exogenous Lactobacilli. These failures are likely due to the poor quality of the commercially available products. It has been documented that Lactobacillus products sold as part of foods or as Lactobacillus supplements are often contaminated with other potential pathogens. In addition, Lactobacillus obtained from yogurt has been shown to be unable to bind to vaginal epithelial cells. The binding of Lactobacilli to the epithelial cells is a necessary step to establish colonization of the host organism. Therefore, the use of commercially available Lactobacillus products is thought to have little utility in prevention or treatment of vaginal infection because the products contain inappropriate microbe strains (e.g., many contain strains which are rarely recovered from the vagina), are contaminated with other potentially pathogenic organisms, have low microbe viability, and/or the microbes typically do not have the ability to bind to vaginal epithelial cells and establish colonization.

Therefore, there is a need for a product for the treatment of vaginal infections which can be manufactured under exacting conditions and which uses appropriate human strains of Lactobacillus having in vivo microbicidal properties, active adherence and an effective potency of viable microbes.

SUMMARY OF THE INVENTION

The present invention generally relates to a bacterium of the genus Lactobacillus with desirable characteristics suitable for use in a vaginal medicant. More particularly, this invention relates to vaginal, rectal and oral medicants having a substantially pure culture of preserved microbial cells, to a preservation matrix and to methods for preventing and treating vaginal infections.

The unique strains of Lactobacillus disclosed herein, when administered in vivo, will colonize and remain affixed to vaginal epithelial cells. These unique strains can then be recovered from the vaginal milieu over time. Such sustained colonization and viability of the Lactobacillus strains is largely attributable to the novel preservation matrix disclosed herein. The protection afforded by the preservation matrix of the present invention allows the Lactobacillus strains to adhere to vaginal epithelial cells in a metabolically inactive state and retain placement while returning to an active state capable of producing functional inhibitory by-products. Such capabilities of a matrix for microbial cells has been heretofore unobserved. The preservation matrix of the present invention also provides the flexibility to allow various drying methods in the production of a commercial suppository product.

One embodiment of the present invention relates to a vaginal medicant. Such a medicant includes a substantially pure bacterial culture of an isolated strain of the genus Lactobacillus having identifying characteristics which include (i) a percent vaginal epithelial cell (VEC) cohesion value (as defined below) of at least about 50% and (ii) an ability to produce greater than about 0.5 ppm of $H_2O_2$ under effective culture conditions. The vaginal medicant of the present invention also includes a preservation matrix, which contains and preserves the bacterial culture. Such a matrix includes a biologically active binding agent, an antioxidant, a polyol, a carbohydrate and a proteinaceous material. In one embodiment, the matrix has a pH of from about 5.0 to about 7.0. In another embodiment, the matrix has a pH of about 7.0. The preservation matrix of the present invention is capable of maintaining at least about $10^6$ viable, genetically stable cells for a period of at least about 12 months in vitro. In further embodiments, the matrix maintains at least about $10^7$ viable cells for a period of at least about 12 months in vitro, and more preferably, at least about $10^8$ viable cells for a period of at least about 12 months in vitro.

In other embodiments, the isolated Lactobacillus strain has a percent VEC cohesion value of at least about 65%, and more preferably, at least about 80% and even more preferably, at least about 95%. In still other embodiments, the isolated strain has an ability to produce at least about 10 ppm of $H_2O_2$, and more preferably, at least about 20 ppm of $H_2O_2$.

As mentioned above, one embodiment of the present invention relates to a strain of Lactobacillus as described above which adheres to vaginal epithelial cells when the strain is in a metabolically inactive state. In another embodiment, the isolated strain sustains colonization of vaginal epithelial cells in vivo for at least about 1 month. In yet another embodiment, the isolated strain maintains genetic stability in vivo for at least about 24 months. A single cell of the isolated strain is from about 1 micron to about 2 microns in width and from about 2 microns to about 4 microns in length and produces at least about 0.75 mg/100 ml of lactic acid under effective culture conditions.

In one embodiment, the Lactobacillus strain of the present invention is of the species *Lactobacillus crispatus*; in another embodiment, the Lactobacillus strain of the present invention is of the species *Lactobacillus jensenii*. In yet another embodiment, a Lactobacillus strain of the present invention has all of the identifying characteristics of *Lactobacillus crispatus* CTV-05, the preferred Lactobacillus strain of the present invention.

The preservation matrix of the present invention maintains at least about $10^6$ viable cells for a period of at least about 12 months in vitro at a temperature from about 4° C. to about 6° C., and preferably at room temperature. In another embodiment, the matrix maintains at least about $10^6$ viable cells for a period of at least about 18 months in vitro, and preferably at least about 24 months in vitro.

The vaginal medicant of the present invention can comprise an inert carrier including, but not limited to, maltodextrin beads or a gelatin capsule. In one embodiment, a gastrointestinal medicant includes (a) a substantially pure bacterial culture of an isolated strain of the genus Lactobacillus having identifying characteristics which include (i) a percent vaginal epithelial cell (VEC) cohesion value (as defined below) of at least about 50% and (ii) an ability to produce greater than about 0.5 ppm of $H_2O_2$ under effective culture conditions; and (b) a preservation matrix, which includes a biologically active binding agent, an antioxidant, a polyol, a carbohydrate and a proteinaceous material. Such a matrix maintains at least about $10^6$ viable, substantially pure and genetically stable cells for a period of at least about 12 months in vitro.

Another embodiment of the present invention relates to a preservation matrix for preserving microbial cells. Such a matrix includes (a) a biologically active binding agent which can include water soluble gum, carboxymethyl cellulose and gelatin; (b) an antioxidant (preferably sodium ascorbate); (c) a polyol which can include xylitol, adonitol, glycerol, dulcitol, inositol, mannitol, sorbitol and arabitol; (d) a carbohydrate which can include dextrose, lactose, maltose, sucrose, fructose, and other monosaccharides, disaccharides and oligosaccharides; and (e) a proteinaceous material which can include skim milk and albumin. Such a matrix maintains at least about $10^6$ viable, substantially pure and genetically stable microbial cells for a period of at least about 12 months in vitro.

In another embodiment, the biologically active binding agent is at least about 10% of the total matrix by weight, the antioxidant is at least about 0.1% of the total matrix by weight, the polyol is at least about 1% of the total matrix by weight, the carbohydrate is at least about 0.5% of the total matrix by weight and the proteinaceous material is at least about 0.5% of the total matrix by weight.

In yet another embodiment, the biologically active binding agent is at least about 14% of the total matrix by weight, the antioxidant is at least about 0.5% of the total matrix by weight, the said polyol is at least about 6% of the total matrix by weight, the carbohydrate is at least about 2.5% of the total matrix by weight and the proteinaceous material is at least about 1.5% of the total matrix by weight.

Another embodiment of the present invention is a preservation matrix for preserving microbial cells which includes about 14% gelatin, about 0.5% sodium ascorbate, about 2.5% dextrose, about 1.5% skim milk and about 6% xylitol, by weight of the preservation matrix.

Yet another embodiment of the present invention relates to a method to prepare a preservation matrix for the preservation of microbial cells. Such a method includes the steps of (a) providing components which include: (i) a sterile biologically active binding agent, which can include water soluble gum, carboxymethyl cellulose and gelatin; (ii) a sterile proteinaceous material which can include skim milk and albumin; (iii) a sterile polyol which can include xylitol, adonitol, glycerol, dulcitol, inositol, mannitol, sorbitol and arabitol;(iv) a sterile antioxidant; (v) a sterile carbohydrate which can include dextrose, lactose, maltose, sucrose, fructose, and other monosaccharides, other disaccharides and other oligosaccharides; and (vi) water; and (b) mixing the components together to form a solution. The biologically active binding agent can be provided as a liquid.

Yet another embodiment of the present invention relates to a method to preserve microbial cells within a preservation matrix. Such a method includes the steps of (a) suspending a culture of at least about $10^6$ microbial cells in a preservation matrix to form a cell matrix suspension; (b) adding the cell matrix suspension to an inert carrier to form a delivery composition; and removing water from the delivery composition. The preservation matrix includes the components as described above. In one embodiment, the method further includes the step of placing the delivery composition into a package which protects the delivery composition from moisture and oxygen during transport and storage.

In one embodiment, the inert carrier can include maltodextrin beads, and the method includes the steps of coating the cell matrix suspension onto the beads and removing water by drying the beads by fluid bed drying.

In another embodiment, the inert carrier includes a gelatin capsule, and the method includes the steps of chilling the gelatin capsule until the cell suspension matrix forms a non-fluid matrix, followed by desiccating the gelatin capsule in a desiccation chamber. The step of desiccating includes providing dry air to the desiccation chamber containing less than about 25% moisture, and more preferably, less than about 15% moisture, and even more preferably, less than about 5% moisture, at a temperature from about 24° C. to about 32° C. and removing humidified air from the chamber. The desiccation chamber can include a compressor, at least one hydrocarbon scrubbing filter and a chilled air compressor. The desiccation chamber can further include a desiccant column.

Yet another embodiment of the present invention relates to a method to protect a female from a vaginal infection. The method includes the step of administering to a female a vaginal medicant of the present invention as previously described herein. Another embodiment relates to a method to treat a vaginal infection, which includes the step of administering to a female a vaginal medicant as previously described herein. Vaginal infections for which such a medicant is useful include bacterial vaginosis, symptomatic yeast vaginitis, gonorrhea, chlamydia, trichomoniasis, human immunodeficiency virus infection, urinary tract infection or pelvic inflammatory disease.

Yet another embodiment of the present invention relates to a method to reduce the risk of infection of a human by human immunodeficiency virus (HIV), which includes the step of administering to a human a medicant of the present invention as previously described herein. Administration of such a medicant can reduce the risk of HIV infection of a human by at least about two-fold.

Another embodiment of the present invention relates to a method to prevent infection of a human by symptomatic yeast vaginitis, which includes administering to a human a vaginal medicant of the present invention as previously described herein. In a preferred embodiment, the Lactobacillus strain included in the medicant is *Lactobacillus crispatus* CTV-05.

Another embodiment of the present invention relates to a method to prevent infection of a human by a gastrointestinal infection, which includes administering to a human a vaginal medicant of the present invention as described herein.

Yet another embodiment of the present invention is a method to prevent preterm birth, which includes administering to a pregnant female a vaginal medicant of the present invention as described herein.

One embodiment of the present invention is a method to enhance metabolism of estrogen in the vagina and bowel, which includes administering to a female a vaginal medicant of the present invention as described herein.

Yet another embodiment of the present invention relates to a vaginal medicant which includes (a) a substantially pure bacterial culture of at least two isolated strains of the genus Lactobacillus having identifying characteristics which include (i) a percent vaginal epithelial cell (VEC) cohesion value (as defined below) of at least about 50% and (ii) an ability to produce greater than about 0.5 ppm of $H_2O_2$ under effective culture conditions; and (b) a preservation matrix, which includes a biologically active binding agent, an antioxidant, a polyol, a carbohydrate and a proteinaceous material. Such a matrix maintains at least about $10^6$ viable, substantially pure and genetically stable cells for a period of at least about 12 months in vitro. Such a medicant can be used to treat at least two vaginal infections which include bacterial vaginosis, symptomatic yeast vaginitis, gonorrhea, chlamydia, trichomoniasis, human immunodeficiency virus infection, urinary tract infection or pelvic inflammatory disease. In one embodiment, the bacterial culture includes a first strain which is effective for treating a first vaginal infection and a second strain which is effective for treating a second vaginal infection. In a preferred embodiment, the first strain is *Lactobacillus crispatus* CTV-05 and the second strain is of the species *Lactobacillus jensenii*.

Another embodiment of the present invention relates to a vaginal medicant which includes (a) a substantially pure bacterial culture of isolated *Lactobacillus crispatus* CTV-05; and (b) a preservation matrix which includes about 14% gelatin, about 0.5% sodium ascorbate, about 2.5% dextrose, about 1.5% skim milk and about 6% xylitol. The matrix maintains at least about 10 viable, genetically stable cells for a period of at least about 12 months in vitro, and preserves desirable characteristics of the *Lactobacillus crispatus* CTV-05. Such characteristics include an ability to adhere to vaginal epithelial cells in a metabolically inactive state, an ability to produce greater than about 0.5 ppm of $H_2O_2$ under effective culture conditions, and a percent vaginal epithelial cell (VEC) cohesion value of at least about 50%.

DETAILED DESCRIPTION OF THE INVENTION

Figure 1:
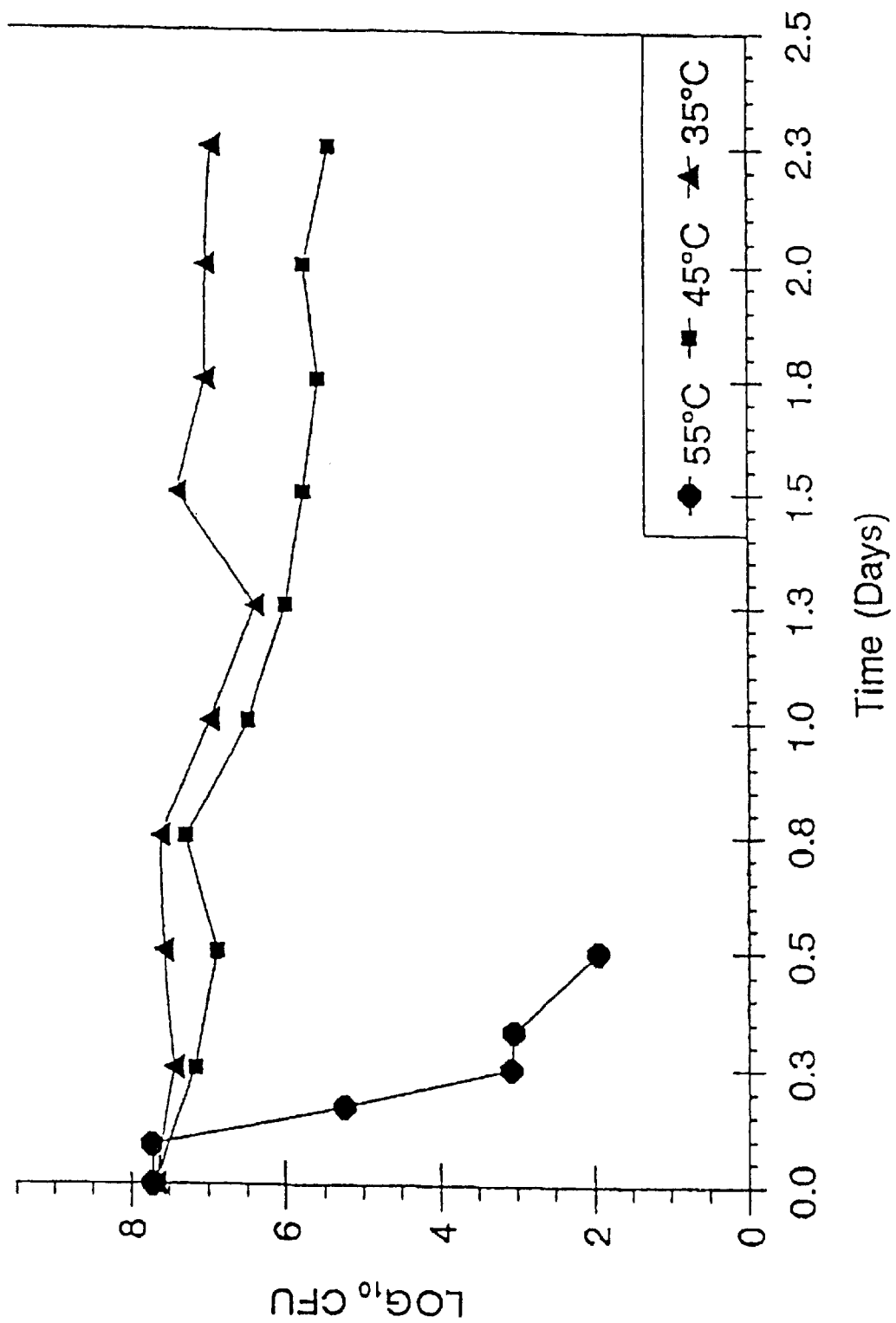
FIG. 1 is a graph showing the effect of elevated temperature storage on the stability of viability of Lactobacillus strain CTV-05.

The present invention generally relates to human strains of bacteria of the genus Lactobacillus which have desirable characteristics suitable for oral use or intravaginal use as a medicant for prophylaxis of vaginal infections. More particularly, the desirable characteristics include the ability to adhere to and colonize vaginal epithelial cells, production of hydrogen peroxide, specific potency, shelf-life stability, inhibition of vaginal infectious agents, production of lactic acid and size of individual microbial cells. Further, this invention relates to a vaginal medicant having a substantially pure culture of preserved microbial cells, and to a method for preserving the microbial cells within the medicant so as to maintain the purity, the genetic stability and the desirable characteristics listed above throughout a storage period of at least about 12 months.

Currently available commercial Lactobacillus products are often contaminated or do not contain appropriate vaginal strains of $H_2O_2$-producing Lactobacilli in sufficient quantities. Furthermore, currently available Lactobacillus strains are often not able to colonize vaginal epithelial cells. In addition to adequate potency and strain selection, existing products may lack efficacy due to the method of preservation employed during their commercial production. In many products, the Lactobacillus strain often loses its ability to adhere to exfoliated vaginal epithelial cells in vitro, and to colonize vaginal epithelial cells in vivo. In addition, the shelf-life of preserved strains is often short, with viable cell counts decreasing rapidly over 2-3 months. Some of the currently used preservation methods were developed for use in the preservation of foods but are perhaps not optimal for preservation of microorganisms. This is critical as the preservation method must protect and suspend the growth of the cells while allowing them to adhere to the vaginal wall in the metabolically inactive state (i.e., the preserved state).

The present invention provides several advantages over the dietary and vaginal supplements that are currently available. Use of modern DNA based technology has suggested that the most common Lactobacillus in the vagina is not *Lactobacillus acidophilus,* which is the species upon which many current dietary supplements and vaginal treatments are based. The present inventors have identified and isolated novel strains of *Lactobacillus crispatus* and *Lactobacillus jensenii* which are superior to any currently available strain for use in a vaginal medicant. Moreover, the present inventors have determined the optimal conditions for producing the strains on both a small and large scale without losing the desirable characteristics during propagation, harvest, preservation, placement in a vaginal delivery system and storage. The present inventors also provide a novel preservation matrix and method for preserving a microbe in a format which enables the preservation of the desirable characteristics of the microbe. More particularly, the preservation matrix of the present invention allows the Lactobacillus strains to adhere to vaginal epithelial cells in vivo in a metabolically inactive state and retain placement while returning to an active state capable of producing functional inhibitory by-products. Such a capability of a microbe/preservation matrix combination has not been described prior to the present invention. The preservation matrix of the present invention also is capable of preserving microbes at room temperature or refrigerated temperatures for long periods of time in storage, and provides the flexibility to allow various drying methods for the production of a commercial medicant. This is the first demonstration of a preservation matrix with such capabilities. The present inventors are unaware of any currently known Lactobacillus vaginal medicant which exhibits efficacy equal to or superior to the efficacy demonstrated by the present medicant both in vitro and in vivo.

According to the present invention, a "vaginal medicant" is a medicant (i.e., medicament or medicine) which is used to prevent or treat infections, diseases, or other disorders directly or indirectly related to the vagina, including infections and diseases which can gain entry to the body through the vagina. Although a vaginal medicant of the present invention is primarily described herein for its use related to vaginal infections, it is to be understood that such a vaginal medicant can be used to treat infections and conditions which are not necessarily related to vaginal infections, such as gastrointestinal infections, in which case a medicant of the present invention can be referred to as a gastrointestinal medicant.

One embodiment of the present invention relates to a vaginal medicant which includes a substantially pure bacterial culture of an isolated strain of the genus Lactobacillus having identifying characteristics which include (i) a percent vaginal epithelial cell (VEC) cohesion value (as defined below) of at least about 50% and (ii) an ability to produce greater than about 0.5 ppm of $H_2O_2$. The vaginal medicant also includes a preservation matrix, which contains and preserves the bacterial culture. Such a matrix includes a biologically active binding agent, an antioxidant, a polyol, a carbohydrate and a proteinaceous material. The matrix is capable of maintaining at least about $10^6$ viable, genetically stable cells for a period of at least about 12 months in vitro. In one embodiment, the vaginal medicant can comprise an inert carrier including, maltodextrin beads or a gelatin capsule.

According to the present invention, an isolated strain of a microbe is a strain that has been removed from its natural milieu. As such, the term "isolated" does not necessarily reflect the extent to which the microbe has been purified. In contrast, a "substantially pure culture" of the strain of microbe refers to a culture which contains substantially no other microbes than the desired strain or strains (i.e., the "suppository strain" or "medicant strain") of microbe. In other words, a substantially pure culture of a strain of microbe is substantially free of other contaminants, which can include microbial contaminants as well as undesirable chemical contaminants.

The presence of the suppository strain or strains and the absence of contaminating strains in a culture can be determined by any method, including by analyzing the microorganisms in a culture for (1) DNA homology using labeled DNA probes, (2) DNA fingerprints and/or (3) cell wall fatty acid profile. For example, strains within a culture can be analyzed for DNA homology to the desired, suppository strains by determining whether DNA from the culture hybridizes under stringent hybridization conditions to DNA from the suppository strain. As used herein, stringent hybridization conditions refer to standard hybridization conditions under which nucleic acid molecules, including oligonucleotides, are used to identify molecules having similar nucleic acid sequences. Stringent hybridization conditions typically permit isolation of nucleic acid molecules having at least about 70% nucleic acid sequence identity with the nucleic acid molecule being used as a probe in the hybridization reaction. Such standard conditions are disclosed, for example, in Sambrook et al., 1989, *Molecular Cloning: A Laboratory Manual,* Cold Spring Harbor Labs Press. The reference Sambrook et al., ibid., is incorporated by reference herein in its entirety. Examples of such conditions include, but are not limited to, the following: Oligonucleotide probes of about 18–25 nucleotides in length with $T_m$'s ranging from about 50° C. to about 65° C. (e.g., DNA from the suppository strain), for example, can be hybridized to nucleic acid molecules (e.g., DNA from the culture to be tested) typically immobilized on a filter (e.g., nitrocellulose filter) in a solution containing 5× SSPE, 1% Sarkosyl, 5× Denhardts and 0.1 mg/ml denatured salmon sperm DNA at 37° C. for about 2 to 12 hours. The filters are then washed 3 times in a wash solution containing 5× SSPE, 1% Sarkosyl at 37° C. for 15 minutes each. The filters can be further washed in a wash solution containing 2× SSPE, 1% Sarkosyl at 37° C. for 15 minutes per wash. Randomly primed DNA probes can be hybridized, for example, to nucleic acid molecules typically immobilized on a filter (e.g., nitrocellulose filter) in a solution containing 5× SSPE, 1% Sarkosyl, 0.5% Blotto (dried milk in water), and 0.1 mg/ml denatured salmon sperm DNA at 42° C. for about 2 to 12 hours. The filters are then washed 2 times in a wash solution containing 5× SSPE, 1% Sarkosyl at 42° C. for 15 minutes each, followed by 2 washes in a wash solution containing 2× SSPE, 1% Sarkosyl at 42° C. for 15 minutes each.

Methods to identify the suppository strain or strains using DNA fingerprinting by Repetitive Sequence Polymerase Chain Reaction (Rep PCR) or using cell wall fatty acid analysis are described in detail below in the Examples section.

A Lactobacillus strain suitable for use in a medicant of the present invention (i.e., a suppository strain) can be any Lactobacillus strain which has the above-described identifying characteristics. Lactobacillus strains can be detected and isolated from natural sources through the use of appropriate screening techniques which are known in the art. The identifying characteristics of Lactobacillus strains suitable for use in the present invention and methods to screen for these characteristics are discussed in detail below. Preferred species of Lactobacillus include *Lactobacillus acidophilus, Lactobacillus jensenii* and *Lactobacillus crispatus,* with *Lactobacillus crispatus* being particularly preferred. Preferably, a suitable strain of Lactobacillus is isolated from the vagina of a human. A particularly preferred strain of Lactobacillus is a strain having all of the identifying characteristics of the *Lactobacillus crispatus* CTV-05 strain, with *Lactobacillus crispatus* CTV-05 being the most preferred.

It is within the scope of the present invention that, in addition to known species and strains of Lactobacillus, newly identified species and strains from nature and mutant strains derived from known or newly identified strains can be used in a medicant of the present invention. Naturally occurring mutants of a parental strain of Lactobacillus that have the identifying characteristics of a Lactobacillus suitable for use in a medicant of the present invention can be isolated by, for example, subjecting a parental strain to at least one round of chemical and/or radiation mutagenesis, in order to increase the rate of mutagenesis, thereby increasing the probability of obtaining a microorganism having improved desired characteristics. It will be obvious to one of skill in the art that mutant microorganisms of the present invention also include microorganisms that can be obtained by genetically engineering microorganisms to, for example, have increased percent VEC cohesion values (defined below). As used herein, a "mutated microorganism" is a mutated parental microorganism in which the nucleotide composition of such microorganism has been modified by mutation(s) that occur naturally, that are the result of exposure to a mutagen, or that are the result of genetic engineering.

One identifying characteristic of a Lactobacillus that is suitable for use in a vaginal medicant of the present invention is that the Lactobacillus strain has a percent vaginal epithelial cell (VEC) cohesion value of at least about 50%, and more preferably at least about 65%, and even more preferably at least about 80%, and most preferably at least about 95%. According to the present invention, the terms "cohesion" and "adherence" can be used interchangeably. Adherence of microbial cells to vaginal epithelial cells is critical for colonization and biological effect. As used herein, colonization refers to the establishment of a site of microbial reproduction on a cell or material which does not necessarily result in tissue invasion or damage. Successful adherence of a Lactobacillus cell of the present invention to a vaginal epithelial cell will result in successful colonization of the vaginal epithelial cell. According to the present invention, "percent VEC cohesion value" is defined as the percentage of VECs to which at least one Lactobacillus cell is adhered in the total number of VECs in an identified group. This is a different measure of adherence than has typically been used in the past. Heretofore, in vitro adherence efficacy has been determined by counting the number of adhered microbial cells on the first pre-defined number (e.g., 50) of vaginal epithelial cells (VECs) observed in a stained preparation and calculating the average, or mean value, of adhered microbial cells per VEC. This mean value has previously served as an indicator of efficacy of a particular strain of microbe. Without being bound by theory, the present inventors believe that determination of "percent VEC cohesion", as described above, is a better measurement of efficacy. The present inventors believe that, with an overall emphasis on the practical perspective, in vitro adherence means nothing if it does not correlate with in vivo adherence and colonization in human subjects. Therefore, rather than using the conventional mean value of adhered cells per VEC in a total count of VECs as a measure of in vitro and in vivo efficacy, the present inventors instead calculate the percentage of VEC cells that have at least one adhered microbial cell in a total count of VECs (i.e., percent VEC cohesion value). The present inventors believe that this value is of greater significance since it is a good predictor of whether a significant number of VECs will accept microbial cells in vitro and in vivo. In contrast, the use of conventional mean values for adherence may be skewed and lead to erroneous interpretations of efficacy. For example, in the following three scenarios in which a technician counts the number of microbial cells adhered to a population of 50 VECs, the two methods of determining adherence (i.e., average adherence versus percent VEC cohesion value) provide surprisingly different evaluations of in vitro adherence efficacy:

A. The technician counts 1500 microbial cells adhered to 10 VECs in a total count of 50 VECs, leaving 40 VECs (80%) with no adhered microbial cells (in this scenario, there are 150 microbial cells on each of the 10 VECs). By conventional mean value calculation, the average adherence value is 30 microbes/cell and the percent VEC cohesion value is 20%.

B. The technician counts 1500 microbial cells adhered to 50 VECs in a total count of 50 VECs, leaving zero VECs (0%) with no adhered microbial cells (in this scenario, there are 30 microbial cells on each of the 50 VECs). By conventional mean value calculation, the average adherence value is again 30 microbes/cell, but the percent VEC cohesion value is 100%.

C. The technician counts 600 microbial cells adhered to a total of 40 VECs in a total count of 50 VECs, leaving 10 VECs (20%) with no adhered microbial cells (in this scenario, there are 15 microbial cells on each of the 40 VECs). By conventional mean value calculation, the average adherence value is 12 microbes/cell, and the percent VEC cohesion value is 80%.

Therefore, using the preferred adherence measurement of the present invention (percent VEC cohesion value), even though the mean number of microbes adhered per VEC is the same in both scenario A and scenario B, the microbes in scenario B would be selected over the microbes of scenario A for their adherence efficacy since more VECs have accepted the microbial cells in scenario B (100% versus 20%). Indeed, even the microbes tested in scenario C would be selected over the microbes of scenario A, because even though the microbes of scenario C have a conventional mean adherence value of 12 microbes/VEC compared to 30 microbes/VEC in scenario A, a greater number of VECs (80% versus 20%) have accepted microbial cells in scenario C. In view of the above scenarios, the percent VEC cohesion value is a more sensitive and relevant calculation of adherence efficacy.

The present inventors believe that a "percent VEC cohesion" value is more predictive of in vivo long-term colonization than the conventional average, or mean, adherence value, especially considering the self-regulation process exhibited by Lactobacilli in the vaginal ecosystem. It has been proposed that overgrowth of $H_2O_2$-producing Lactobacilli in the vagina is prevented by self-inhibition when the Lactobacilli population becomes "over crowded". This built-in safety factor minimizes the possibility of detrimental effects of excessive numbers of vaginal Lactobacilli. Considering this phenomenon, in the present invention, a suppository strain which will spread itself over a larger range of VECs (e.g., has a high percent VEC cohesion value) is preferred over a strain that would adhere in large numbers to only a few VECs. It is likely that the latter situation may lead to self-inhibition of $H_2O_2$-producing Lactobacilli on a few over-crowded VECs, thus decreasing the likelihood for long-term survival and colonization of the microbe. Long-term in vivo colonization is the ultimate objective of the products and methods of the present invention and it is believed that smaller numbers of Lactobacilli cells adhered to a larger number of VECs will better achieve this objective. In one embodiment, an isolated Lactobacillus strain for use in a medicant of the present invention is identified by its ability to sustain colonization of vaginal epithelial cells for at least about 1 month.

Another identifying characteristic of a Lactobacillus which is suitable for use in a medicant of the present invention is the ability to produce hydrogen peroxide ($H_2O_2$). As discussed above, hydrogen peroxide has been shown to be directly responsible for the killing of other microorganisms by the Lactobacillus. Preferably, the Lactobacillus is able to produce greater than about 0.5 ppm of $H_2O_2$ under normal growth conditions. More preferably, the Lactobacillus is able to produce at least about 10 ppm of $H_2O_2$, and even more preferably, the Lactobacillus is able to produce at least about 20 ppm of $H_2O_2$ under effective growth conditions, herein defined as any medium and conditions capable of promoting production of $H_2O_2$. Effective growth conditions include both in vitro growth conditions (e.g., an effective culture medium and conditions) and in vivo growth conditions (e.g., successful colonization of a vaginal epithelial cell).

$H_2O_2$ production by a Lactobacillus of the present invention can be quantitated by any means for measuring $H_2O_2$ production. For example, $H_2O_2$ production can be measured by quantitation of the intensity of a blue pigment formed when Lactobacillus is inoculated onto tetramethylbenzidine medium (TMB) and incubated under anaerobic conditions. $H_2O_2$ production can also be measured using commercially available $H_2O_2$ detection strips (e.g., available from EM Sciences).

In one embodiment, another identifying characteristic of a Lactobacillus suitable for use in a medicant of the present invention is the genetic stability of the Lactobacillus over time both in vivo and in vitro. According to the present invention, genetic stability refers to the ability of successive generations of a Lactobacillus strain to substantially maintain the identical genetic profile of the mother strain. In other words, successive generations of a genetically stable strain will not acquire substantial mutations in its DNA over a period of time. More importantly, successive generations of a genetically stable strain will not acquire substantial mutations in DNA related to one of the above described identifying characteristics over time. Most importantly, successive generations of a genetically stable strain will not acquire substantial mutations (e.g., mutations that significantly change the phenotype of the encoded protein) in DNA related to the identifying characteristics of vaginal epithelial cell cohesion value, hydrogen peroxide production, or the ability to adhere to vaginal epithelial cells in a metabolically inactive state as described herein. Preferably, a Lactobacillus strain of the present invention which has colonized vaginal epithelial cells in vivo will maintain genetic stability in vivo for at least about 12 months of vaginal colonization, and more preferably at least about 18 months, and even more preferably at least about 24 months of vaginal colonization. In vitro, the genetic stability of a microorganism can be affected by the culturing conditions of the microorganism and by the preparation and storage format of the vaginal medicant of the present invention. Such conditions are discussed in detail below. Due to the superior qualities of the preservation matrix of the present invention, a Lactobacillus strain of the present invention preserved in a preservation matrix of the present invention is preferably genetically stable for at least about 12 months in vitro, and more preferably, at least about 18 months in vitro and even more preferably at least about 24 months in vitro during storage at room temperature or at refrigeration temperature (2–8° C.). Genetic stability can be evaluated by any method of evaluating mutations or identifying selectable genetic markers. For example, genetic marker profiles based on restriction endonuclease patterns can be performed to establish the stability of genetic profile of a particular culture compared to the mother strain. Repetitive Sequence Polymerase Chain Reaction (Rep PCR) has been used by the present inventors to distinguish as many as 40 different strains of Lactobacillus from each other, and to confirm genetic stability of a particular strain of Lactobacillus over time after either in vitro storage or in vivo colonization of vaginal epithelial cells.

In one embodiment, an identifying characteristic of a Lactobacillus suitable for use in a medicant of the present invention is the ability to produce lactic acid. Lactic acid has been shown to inhibit the growth of pathogens in vitro. Preferably, a Lactobacillus produces at least about 0.75 mg/100 ml lactic acid, and more preferably at least about 4 mg/100 ml lactic acid, and even more preferably at least about 8.8 mg/100 ml lactic acid under effective growth conditions.

In another embodiment of the present invention, a suitable Lactobacillus strain has a relatively large cell size. Ranges of typical Lactobacilli as provided in Bergey's Manual of Determinative Bacteriology are 0.8–1.6 $\mu$m (width)×2.3–11 $\mu$m (length). A preferred Lactobacillus strain for use in the present invention has a cell size of from about 1 to about 2 microns in width and from about 2 to about 4 microns in length. Without being bound by theory, the present inventors believe that the large dimensions exhibited by cells of a Lactobacillus strain of the present invention may allow it to better serve as a protective agent in biocompetitive exclusion. Biocompetitive exclusion refers to the ability of the suppository strain or strains of the present invention to competitively inhibit the growth of undesired bacterial strains. Such exclusion is attributed to the occupation of available space on a vaginal epithelial cell by the beneficial Lactobacilli cells (e.g., the suppository strain), thus preventing attachment of pathogenic, or undesirable, microbial cells.

A vaginal medicant of the present invention also includes a preservation matrix. Microbial cells are suspended in the preservation matrix for preservation and storage in the delivery format. This matrix, as well as the microbial culture media, the methods of harvesting microbial cells and the preservation process, all have a profound effect on cell viability during storage and performance of the preserved cells after rehydration (e.g., rehydration in the vagina). The preservation matrix of the present invention maintains all of the previously described desirable characteristics of the vaginal strain.

The preservation matrix of the present invention is comprised of ingredients to minimize the damaging effects encountered during the preservation process and to provide functional properties. As will be discussed in detail below, when a Lactobacillus strain of the present invention is added to the preservation matrix for preservation, it is preferably converted from an actively growing metabolic state to a metabolically inactive state. One further identifying characteristic of a Lactobacillus strain used in a vaginal medicant of the present invention is that it is able to adhere to vaginal epithelial cells even when in a metabolically inactive state. The preservation matrix of the present invention is therefore also formulated for optimal microbial cell resilience, such that upon rehydration in vivo, the microbial cells are immediately free to adhere to vaginal epithelial cells and then return to full metabolic activity without delay.

The preservation matrix of the present invention includes a biologically active binding agent, an antioxidant, a polyol, a carbohydrate and a proteinaceous material. It is to be noted that the term "a" or "an" entity refers to one or more of that entity; for example, a carbohydrate refers to one or more carbohydrates or at least one carbohydrate. As such, the terms "a" (or "an"), "one or more" and "at least one" can be used interchangeably herein. It is also to be noted that the terms "comprising", "including", and "having" can be used interchangeably.

According to the present invention, a biologically acceptable binding agent is binding agent, preferably a protein, which is acceptable for use in vivo (e.g., does not have any activity or toxic effect in vivo), which affixes the cell matrix to an inert carrier (described below) during the preservative process and which provides protective effects (i.e., maintains cell viability) throughout preservation and storage of the microbial cells. Preferred biologically acceptable binding agents for use in a preservation matrix of the present invention include, but are not limited to a water-soluble gum, carboxymethyl cellulose and/or gelatin. A biologically acceptable binding agent typically comprises from about 10% to about 20% by weight of the preservation matrix, and preferably comprises about 14% by weight of the preservation matrix. In one embodiment, a preservation matrix of the present invention comprises about 14% gelatin by weight of the preservation matrix.

Antioxidants included in a preservation matrix of the present invention are provided to retard oxidative damage to the microbial cells during the preservation and storage process. A particularly preferred antioxidant is sodium ascorbate. An antioxidant typically comprises from about 0.1% to about 1.0% by weight of the preservation matrix, and preferably comprises about 0.5% by weight of the preservation matrix. In one embodiment, a preservation matrix of the present invention comprises about 0.5% sodium ascorbate by weight of the preservation matrix.

Polyols (i.e., polyhydric alcohols) included in a preservation matrix of the present invention are provided to maintain the native, uncollapsed state of cellular proteins and membranes during the preservation and storage process. In particular, polyols interact with the cell membrane and provide support during the dehydration portion of the preservation process. Preferred polyols include, but are not limited to xylitol, adonitol, glycerol, dulcitol, inositol, mannitol, sorbitol and/or arabitol. A polyol typically comprises from about 1% to about 12% by weight of the preservation matrix, and preferably comprises about 6% by weight of the preservation matrix. In one embodiment, a preservation matrix of the present invention comprises about 6% xylitol by weight of the preservation matrix.

Carbohydrates included in a preservation matrix of the present invention are provided to maintain the native, uncollapsed state of cellular proteins and membranes during the preservation and storage process. In particular, carbohydrates provide cell wall integrity during the dehydration portion of the preservation process. Preferred carbohydrates include, but are not limited to dextrose, lactose, maltose, sucrose, fructose and/or any other monosaccharide, disaccharide or polysaccharide. A carbohydrate typically comprises from about 0.5% to about 5% by weight of the preservation matrix, and preferably comprises about 2.5% by weight of the preservation matrix. In one embodiment, a preservation matrix of the present invention comprises about 2.5% dextrose by weight of the preservation matrix.

A proteinaceous material included in a preservation matrix of the present invention provides further protection of the microbial cell during the dehydration portion of the preservation process. Preferred proteinaceous materials include, but are not limited to skim milk and albumin. A proteinaceous material typically comprises from about 0.5% to about 5% by weight of the preservation matrix, and preferably comprises about 1.5% by weight of the preservation matrix. In one embodiment, a preservation matrix of the present invention comprises about 1.5% skim milk by weight of the preservation matrix.

In one embodiment of the present invention, a preservation matrix includes a biologically active binding agent that is at least about 10% of the preservation matrix by weight, an antioxidant that is at least about 0.1% of the preservation matrix by weight, a polyol that is at least about 1% of the preservation matrix by weight, a carbohydrate that is at least about 0.5% of the preservation matrix by weight, and a proteinaceous material that is at least about 0.5% of the preservation matrix by weight.

A particularly preferred preservation matrix of the present invention comprises about 14% gelatin, about 0.5% sodium ascorbate, about 2.5% dextrose, about 1.5% skim milk and about 6% xylitol, by weight of the preservation matrix.

The pH of the preservation matrix is important for optimal stability of the preserved microbial cells. The optimal pH of the preservation matrix can be determined by preparing suspensions of Lactobacilli cells in matrices adjusted to various pHs. A preservation matrix of the present invention is typically from about pH 5.0 to about pH 7.0, and preferably, about pH 7.0.

The preservation matrix for use in a vaginal medicant of the present invention, in addition to the particular qualities described above, maintains at least about $10^6$ viable, substantially pure and genetically stable cells in vitro for a period of at least about 12 months. As discussed above, the term "substantially pure" refers to a culture of microbial cells of the present invention which are substantially free of any other undesirable microorganisms (e.g., contaminants). The importance of genetic stability of such cells has also been discussed previously herein. In a more preferred embodiment, a preservation matrix of the present invention is capable of maintaining at least about $10^7$, and even more preferably, at least about $10^8$ viable, substantially pure and genetically stable Lactobacillus cells for a period of at least about 12 months.

In another embodiment of the present invention, a preservation matrix used in a medicant of the present invention is preferably capable of maintaining at least about $10^6$ viable, substantially pure and genetically stable Lactobacillus cells for a period of at least about 18 months, and even more preferably for a period of at least about 24 months.

Vaginal medicants of the present invention can be stored either at room temperature or at refrigerated temperature, which is typically from about 4° C. to about 6° C. In yet another embodiment, a preservation matrix used in a medicant of the present invention is preferably capable of maintaining at least about $10^6$ viable, substantially pure and genetically stable Lactobacillus cells for a period of at least about 12 months at room temperature. In another embodiment, a preservation matrix used in a medicant of the present invention is preferably capable of maintaining at least about $10^6$ viable, substantially pure and genetically stable Lactobacillus cells for a period of at least about 12 months at refrigerated temperature.

The ability of the matrix to preserve a minimum number of viable cells is critical to the efficacy of the medicant of the present invention and has been particularly problematic in vaginal treatments prior to the present invention. More specifically, the number of viable, substantially pure, genetically stable cells that are delivered in a medicant unit (e.g., a single suppository or tablet) is directly related to the critical issue of potency of the medicant. As used herein, the term "efficacy" refers to the ability of a suppository strain to exhibit a biological effect (e.g., provide a statistically significant level of protection against vaginal infection). "Potency" directly relates to the number of viable microbial cells delivered per medicant unit (i.e., per suppository or tablet). According to the present invention, viable cells have the ability to grow and reproduce. For a Lactobacillus medicant to be efficacious in vivo, both colonization of the vaginal epithelial cells by the microbial cells at a potency of at least about $10^6$ and biological effect (e.g., as evidenced by absence of an infected state such as bacterial vaginosis) are necessary. The present inventors have discovered that there is a difference between the potency of a medicant that allows colonization of the suppository strain and the potency of a medicant which exhibits a biological effect. The present inventors have found that the ability of the suppository strain to colonize vaginal epithelial cells combined with the specific potency requirements for a biological effect are critical for an efficacious Lactobacillus medicant. More specifically, a concentration of viable microbial cells that results in vaginal colonization of the suppository strain is necessary, but may not be sufficient, for a medicant to be efficacious.

For example, good colonization of vaginal epithelial cells can be achieved at very low potencies (e.g., $10^5$ microbial cells) using the Lactobacillus strains and preservation format of the present invention. However, biological effect is not demonstrated at this potency. Therefore, colonization of vaginal epithelial cells is necessary for a biological effect, but colonization in the absence of insufficient potencies will not lead to the numerical superiority necessary to demonstrate biologic effect. The preservation matrix of the present invention demonstrates the heretofore unobserved ability to maintain the necessary potency of biologically effective Lactobacillus cells both in vitro over extended periods of time and in vivo upon delivery to vaginal epithelial cells.

Another embodiment of the present invention relates to a method to make a preservation matrix as previously described herein. Such a method includes the steps of (a) providing components which include: (i) a sterile biologically active binding agent, which can include water soluble gum, carboxymethyl cellulose or gelatin; (ii) a sterile proteinaceous material which can include skim milk or albumin; (iii)a sterile polyol which can include xylitol, adonitol, glycerol, dulcitol, inositol, mannitol, sorbitol or arabitol; (iv) a sterile antioxidant; (v) a sterile carbohydrate which can include dextrose, lactose, maltose, sucrose, fructose, and other monosaccharides, other disaccharides and other oligosaccharides; and(vi) water; and (b) and mixing said components together to form a solution. The biologically active binding agent is provided in a liquid form, which typically requires heating of the agent to about 37° C., since such agents are likely to be in solid phase at room temperature. The various components of the preservation matrix and the preferred amounts of each are discussed in detail above. The components of the preservation matrix can be sterilized by any suitable method of sterilization. In a preferred embodiment, the biologically active binding agent and the proteinaceous material are sterilized by autoclave and the polyol, carbohydrate and antioxidant are sterilized by filtration. After the components are mixed to form a preservation matrix solution, such a solution can be used immediately, held at 37° C. for short periods of time, or frozen at about −20° C.

In a preferred embodiment, a vaginal medicant of the present invention includes an inert carrier. According to the present invention, an inert carrier can be any inert material which is suitable for use in vivo and which can be used to carry or support the cell suspension matrix (i.e., preservation matrix combined with microbial cells) of the present invention in such a manner that the cell suspension matrix can be stored in vitro and/or administered in vivo. Inert carriers include, but are not limited to, maltodextrin beads and gelatin capsules. Such carriers are discussed in more detail below.

One embodiment of the present invention relates to a vaginal medicant which includes (a) an isolated, substantially pure bacterial culture of *Lactobacillus crispatus* CTV-05; (b) a preservation matrix, which includes about 14% gelatin, about 0.5% sodium ascorbate, about 2.5% dextrose, about 1.5% skim milk and about 6% xylitol. The preservation matrix maintains at least about $10^6$ viable, genetically stable cells in vitro for a period of at least about 12 months. In addition, the preservation matrix preserves the desirable characteristics of the *Lactobacillus crispatus* CTV-05. Such characteristics include, for example, an ability to adhere to vaginal epithelial cells in a metabolically inactive state, an ability to produce greater than about 0.5 ppm of $H_2O_2$ under effective culture conditions, or a percent vaginal epithelial cell (VEC) cohesion value of at least about 50%. These characteristics have been discussed in detail above.

Another embodiment of the present invention relates to a vaginal medicant which includes a substantially pure bacterial culture of at least two different isolated strains of the genus Lactobacillus having identifying characteristics which include (i) a percent vaginal epithelial cell (VEC) cohesion value of at least about 50% and (ii) an ability to produce greater than about 0.5 ppm of $H_2O_2$ under effective culture conditions. The vaginal medicant also includes a preservation matrix, which contains and preserves the bacterial culture. Such a matrix includes a biologically active binding agent, an antioxidant, a polyol, a carbohydrate, and a proteinaceous material. The matrix is capable of maintaining at least about $10^6$ viable, genetically stable cells for a period of at least about 12 months in vitro. In one embodiment, the vaginal medicant can also include an inert carrier.

In this embodiment of the present invention, each of the Lactobacillus strains is selected for its ability to prevent and/or treat a vaginal infection which is different from the vaginal infection prevented or treated by the other Lactobacillus strains included in the medicant. Such infections can include, but are not limited to, bacterial vaginosis, symptomatic yeast vaginitis, gonorrhea, chlamydia, trichomoniasis, human immunodeficiency virus infection, urinary tract infection and pelvic inflammatory disease. For example, in a preferred embodiment, a vaginal medicant includes a first Lactobacillus strain which is useful for preventing bacterial vaginosis, and a second Lactobacillus strain which is useful for preventing symptomatic yeast vaginitis. In a preferred embodiment, a first Lactobacillus strain is *Lactobacillus crispatus* CTV-05 and a second Lactobacillus strain is a strain of *Lactobacillus jensenii*.

Another embodiment of the present invention relates to an isolated bacterial strain of the genus Lactobacillus. Such a strain has identifying characteristics which include (a) a percent vaginal epithelial cell (VEC) cohesion value of at least about 50% and (b) an ability to produce greater than about 0.5 ppm of $H_2O_2$. In another embodiment, such an isolated strain preferably has a percent VEC cohesion value of at least about 65%, and more preferably of at least about 80% and even more preferably of at least about 95%. In further embodiments, such a strain preferably produces at least about 10 ppm of $H_2O_2$, and even more preferably at least about 20 ppm of $H_2O_2$.

An isolated bacterial strain of the genus Lactobacillus of the present invention can have one or more other desirable identifying characteristics. Such characteristics have been previously described herein. In particular, in one embodiment, an isolated bacterial strain of the genus Lactobacillus is able to sustain colonization of vaginal epithelial cells for at least about 1 month. In another embodiment, an isolated bacterial strain of the genus Lactobacillus maintains genetic stability over at least about 24 months of vaginal colonization. In yet another embodiment, such a strain adheres to vaginal epithelial cells when the strain is in a metabolically inactive state (i.e., when in a preserved state). A further identifying characteristic of such a strain is the ability of the strain to produce at least about 0.75 mg/100 ml of lactic acid under effective growth conditions. In yet another embodiment, such a strain is from about 1 micron to about 2 microns in width and from about 2 microns to about 4 microns in length.

In a preferred embodiment, such an isolated bacterial strain is isolated from the human vagina. In another preferred embodiment, the strain is of the species *Lactobacillus crispatus* or *Lactobacillus jensenii*. A particularly preferred strain has all of the identifying characteristics of *Lactobacillus crispatus* CTV-05, with *Lactobacillus crispatus* CTV-05 being the most preferred strain.

Yet another embodiment of the present invention relates to a bacterial strain of Lactobacillus which has substantially all of the identifying characteristics of *Lactobacillus crispatus* CTV-05. Such a strain is particularly useful for protecting a female from a vaginal infection.

One embodiment of the present invention relates to a method to preserve microbial cells within a preservation matrix to form a vaginal medicant. This method includes the steps of (a) suspending a culture of at least about $10^6$ microbial cells in a preservation matrix which includes a biologically active binding agent, an antioxidant, a polyol, a carbohydrate and a proteinaceous material, to form a cell matrix suspension; (b) adding the cell matrix suspension to an inert carrier to form a delivery composition; and removing water from the delivery composition.

In a further embodiment of this method, the delivery compositions can be placed into a package to protect against moisture and oxygen during transport and storage. The package can be any suitable material for such protection such as Mylar or metallic film pouches. In one embodiment, the delivery compositions can be packaged in individual packages. Another embodiment may include packaging with multiple cavities, perhaps aligned with dosage.

Conventional methods of preserving microbial cells commonly employ air drying, spray drying or freeze drying. Air drying requires long periods of time, sometimes with somewhat elevated temperatures. Spray drying exposes the cells to hot air, turbulence and excessive levels of oxygen. Freeze drying requires dramatic fluctuations in temperature and the inherent risk of ice crystal formation. An advantage of the preservation matrix of the present invention is that the matrix allows removal of water from the cells by a variety of conventional drying methods with minimal damage to the microbial cells. Preferably, the method of producing the vaginal medicant of the present invention encompasses processing steps which are most likely to reduce stress to the cells during harvest, dispensing and preservation so as to maximize the likelihood of a final product with long shelf-life and capability of delivering viable cells of the suppository Lactobacillus strain having the desirable characteristics described above. Stresses to avoid include an excessive number of processing steps, fluctuations of temperature, use of vacuum, exposure to moisture and long processing times. The process preferably also limits the introduction of contaminating microorganisms, a common problem in existing commercial preparations of Lactobacilli. Particularly preferred methods of preserving microbial cells in a preservation matrix are discussed in detail below.

All methods of microorganism preservation require drying or removal of water. Water in microorganisms exists in both free and bound states. Removal of sufficient amounts of both states is necessary for preservation of the microorganism, but excessive removal of the bound water may be problematic. Other problematic factors in the preservation process include the amount of time employed to remove the cellular moisture and the temperature of the process. Generally, it is preferred to remove moisture quickly with careful attention to temperature control, particularly if higher temperatures are used.

The present invention provides an optimal method for preservation of microorganisms which is designed to (1) be able to accept the microbial cells in a protective matrix wherein the cells are added to the matrix immediately after they are harvested from the culture medium; (2) avoid exposure of cells to temperatures above 40° C. at any time during the preservation process; (3) avoid exposure of cells to ice crystal formation; (4) avoid exposure of cells to high or low extremes in temperature fluctuation; (5) have a short duration of the preservation process, optimally less than 4 hours; (6) avoid exposure of cells to vacuum or compression; and (7) avoid exposure of cells to air that may carry contaminating microorganisms. The goal of the preservation method is to have the final medicant product rehydrated directly within the vaginal milieu.

In one embodiment, the method of preserving microbial cells within a preservation matrix includes coating the cell matrix suspension onto an inert carrier which preferably is a maltodextrin bead. The coated beads are then dried, preferably by a fluid bed drying method. Fluid bed drying methods are well known in the art. For example, maltodextrin beads are placed into a fluid bed dryer are dried at 33° C. The air pressure is set to 14 psi, the cell suspension matrix is sprayed onto the beads and the heat is increased to 38° C. The coated beads are then allowed to dry for an additional period of time. The coated maltodextrin beads can be stored as a powder, placed into gelatin capsules, or pressed into tablets.

In another embodiment of the present invention, a convenient suppository format for delivering viable Lactobacillus cells of the present invention in an exogenous fashion to the vaginal milieu is that of a hard gelatin capsule. Gelatin capsules are commercially available and are well known in the art. In this embodiment, the above preservation method further comprises dispensing the cell suspension matrix to a gelatin capsule, chilling the gelatin capsule until the cell suspension matrix forms a non-fluid matrix and to affix the gel to the interior wall of the gelatin capsule, and desiccating the gelatin capsule in a desiccation chamber. The step of dispensing can be accomplished by any means known in the art, and includes manual, semi-automated and automated mechanisms. The chilling step is performed at from about 4° C. to about 6° C. The step of desiccating the gelatin capsule can include the steps of (i) providing dry air to the desiccation chamber containing less than about 25% moisture, at a temperature from about 24° C. to about 32° C.; and (ii) removing humidified air from the desiccation chamber.

In this embodiment, the desiccation process can proceed for about 1 to about 6 hours. The desiccation chamber can include a compressor, at least one hydrocarbon scrubbing filter and a chilled air compressor with or without a desiccant silica gel (or any other suitable desiccant material) column, in series. It is a preferred embodiment that the air entering the chamber (dry air) should contain less than about 25% moisture, and more preferably less than about 15% moisture, and even more preferably less than about 5% moisture, down to as little as zero moisture. The dry air should preferably have a temperature from about 24° C. to about 32° C. The preferred rate of air flow is 2 air exchanges per minute. This method allows preservation of microbial cells in a controlled environment with room temperature air in a short period of time. Also, the microbial cells may be dispensed directly into the suppository delivery device and preserved in an in situ fashion in the same device, thus increasing the likelihood of maintaining desirable identifying characteristics of the microbial cell.

One step of the method for preserving microbial cells in a matrix includes suspending a culture of microbial cells in a preservation matrix. According to the present invention, microbial cells are harvested from the culture medium and immediately suspended in the preservation matrix at optimal cell matrix ratio. Optimally but not necessarily, the harvest and suspension process is accomplished within a Class 100 environment.

Lactobacillus cells of the present invention can be grown in any medium which provides effective growth of the microbe without contamination, loss of genetic stability, or loss of any other desirable identifying and functional characteristics of a Lactobacillus strain of the present invention (as previously described herein). More particularly, Lactobacillus strains of the present invention are grown in a culture medium which includes a source of assimilable organic carbon, a source of assimilable nitrogen and appropriate salts and trace metals. A preferred medium for culturing Lactobacillus strains of the present invention is MRS medium. MRS medium is described in detail in the Examples section.

The Lactobacillus microorganisms of the present invention can be cultured in conventional culture conditions, which include, but are not limited to agar surface culture or broth fermentation. Both agar surface culture and broth fermentation methods are well known in the art. The Lactobacillus are preferably cultured anaerobically or microaerophilically.

The temperature of the culture medium can be any temperature suitable for growth of Lactobacillus. For example, prior to inoculation of the culture medium with an inoculum, the culture medium can be brought to and maintained at a temperature in the range of from about 20° C. to about 35° C., and more preferably in the range of from about 25° C. to about 35° C.

The culture medium is inoculated with an actively growing culture of a Lactobacillus strain of the present invention in an amount sufficient to produce, after a reasonable growth period, a suitable cell density for transfer to the preservation matrix. Typical inoculation cell densities are within the range of from about $10^6$ CFUs/ml to about $10^9$ CFUs/ml, and more preferably from about $10^8$ CFUs/ml to about $10^9$ CFUs/ml, based on the dry weight of the cells. The cells are then grown to a cell density in the range of from about $10^7$ CFUs/ml to about $10^9$ CFUs/ml, and more preferably to about $10^8$ CFUs/ml. At this stage, the cells are harvested for preservation in the preservation matrix.

In the first step of this embodiment of the present invention, after reaching the desired cell density, the microbial cells are harvested, preferably by a method such as centrifugation. At least about $10^7$ microbial cells, and more preferably at least about $10^8$ microbial cells and even more preferably at least about $10^9$ microbial cells are suspended in a preservation matrix. Prior to addition of the cells to the matrix, the cells may be washed in a saline buffer. The preservation matrix and microbial cell mixture is referred to herein as the cell suspension matrix. The cell suspension matrix is typically maintained at 30–40° C. with continuous mixing during the subsequent steps of adding the matrix to an inert carrier. It is to be understood that one of ordinary skill in the art will appreciate variations to the basic culturing, harvesting and suspending steps disclosed herein and as such, the present invention incorporates such variations.

Yet another embodiment of the present invention relates to a method to protect a female against vaginal infections. This method includes administering to a female a vaginal medicant which includes (a) a substantially pure bacterial culture of at least about $10^6$ isolated strain of the genus Lactobacillus having identifying characteristics which include (i) a percent VEC cohesion value of at least about 50% and (ii) an ability to produce greater than about 0.5 ppm of $H_2O_2$. The medicant also includes (b) a preservation matrix which includes a biologically active binding agent, an antioxidant, a polyol, a carbohydrate and a proteinaceous material. In a further embodiment, the vaginal medicant can include an inert carrier as described previously herein. The preservation matrix maintains at least about $10^6$ viable, substantially pure and genetically stable cells for a period of at least about 12 months in vitro.

Many of the above embodiments have been described previously herein in detail. The vaginal medicant of the present invention can be used to prevent a variety of vaginal infections, including, but not limited to bacterial vaginosis, symptomatic yeast vaginitis, gonorrhea, chlamydia, trichomoniasis, human immunodeficiency virus infection, urinary tract infection and pelvic inflammatory disease.

According to the present invention, "to protect a female from a vaginal infection" refers to reducing the potential for a female to develop a vaginal infection. Preferably, the potential for a vaginal infection is reduced, optimally, to an extent that the female does not suffer discomfort and/or altered function from exposure to a vaginal infectious agent. For example, protecting a female from a vaginal infection can refer to the ability of a vaginal medicant of the present invention, when administered to the female, to prevent a vaginal infection from occurring or recurring.

Another embodiment of the present invention relates to a method to treat a vaginal infection by administering to a female having a vaginal infection a vaginal medicant of the present invention. As used herein, treating a female with a vaginal infection refers to the ability of a vaginal medicant of the present invention to cure or alleviate infection symptoms, signs or causes.

Preferably, a single vaginal medicant to be administered to a female to prevent or to treat a vaginal infection includes at least about $10^6$ and more preferably at least about $10^7$ and even more preferably, at least about $10^8$ viable, substantially pure and genetically stable Lactobacillus cells having the identifying characteristics described herein. A preferred administration protocol includes the dose and the frequency of administration of the medicant and can be readily determined by one of skill in the art. In one embodiment, a single medicant is administered at least about once a day for about two days, or in another embodiment, at least about once a day for about three days, or in another embodiment, at least about twice a day for about three days. Such dosage can be administered again, if needed, for example, on a monthly basis. A vaginal medicant of the present invention can be administered orally, vaginally or rectally, although any other modes of administration which can deliver the microorganisms to the desired site of action are encompassed herein. A preferred format for administration is a suppository (e.g., such as a tablet or a capsule).

A vaginal medicant of the present invention can be administered in conjunction with (e.g., simultaneously with, before, and/or after) any other therapy for the prevention or treatment of vaginal infections. For example, a vaginal medicant can be administered in conjunction with an antibiotic.

Another embodiment of the present invention relates to a method to reduce the risk of infection of a human by human immunodeficiency virus (HIV) by administering to a human a medicant of the present invention as described herein. Preferably, the medicant reduces the risk of HIV infection by the human by at least about 2-fold, and more preferably, at least about 4-fold, and even more preferably, by at least about 6-fold. The human to which such a medicant can be administered can be a male or a female. The medicant can be administered orally, vaginally or rectally to a female, and orally or rectally to a male. In a preferred embodiment, a single medicant is administered daily for two days.

Yet another embodiment of the present invention is a method to prevent symptomatic yeast vaginitis by administering to a human a medicant of the present invention as described herein. In a preferred embodiment, such a medicant includes *Lactobacillus crispatus* CTV-05.

Another embodiment of the present invention is a method to prevent preterm birth. As discussed previously herein, bacterial vaginosis is one of the most common genital infections in pregnancy. Women with bacterial vaginosis diagnosed during the second trimester of pregnancy are 40 percent more likely to give birth to a premature, low-birth—weight infant than women without bacterial vaginosis. A method to prevent preterm births according to the present invention includes the steps of administering to a pregnant female (a) antibiotics and (b) a vaginal medicant of the present invention as described herein. Preferred dosages are as described above for administration of a vaginal medicant to prevent a vaginal infection. Preferred antibiotics to be administered with a vaginal medicant of the present invention include any antibiotic useful in treating vaginal infections. Such antibiotics are known in the art.

Another embodiment of the present invention includes a method to assist metabolism of estrogen in the vagina and bowel. Hyperestrogenism is a condition afflicting women which can be treated using a medicant of the present invention. The Lactobacillus strains of the present invention appear to assist in proper metabolism of estrogen in the vagina and the bowel. This method includes the step of administering to a female a medicant of the present invention as described herein. Such a medicant can be administered vaginally, orally, or rectally. Dosage ranges are substantially similar to those provided herein for treatment of vaginal infections.

As mentioned above, although the above discussion of the medicant of the present invention has been primarily directed to the use of such a medicant to treat vaginal infections, a medicant of the present invention is not restricted for use in the treatment of infections of or related to the vagina. A medicant of the present invention can be used, for example, to treat a gastrointestinal disorder or infection. In this case, such a medicant is referred to as a gastrointestinal medicant. A gastrointestinal medicant of the present invention has all of the distinguishing features of a vaginal medicant of the present invention, including a substantially pure bacterial culture of an isolated strain of the genus Lactobacillus having identifying characteristics which include (i) a percent vaginal epithelial cell (VEC) cohesion value of at least about 50% and (ii) an ability to produce greater than about 0.5 ppm of $H_2O_2$. In another embodiment, an initial strain useful in the treatment of gastrointestinal infection has VEC cohesion values and/or $H_2O_s$ production values less than those useful in the vagina while still retaining effective gastrointestinal medicant qualities. The gastrointestinal medicant also includes a preservation matrix, which contains and preserves the bacterial culture. Such a matrix includes a biologically active binding agent, an antioxidant, a polyol, a carbohydrate and a proteinaceous material. The matrix is capable of maintaining at least about $10^6$ viable, genetically stable cells for a period of at least about 12 months in vitro. The gastrointestinal medicant can comprise an inert carrier including, maltodextrin beads or a gelatin capsule. A medicant for use in the gastrointestinal tract is administered by any route by which the microorganisms of the medicant can reach and adhere to cells in the gastrointestinal tract. Such modes of delivery include, but are not limited to oral and rectal delivery.

The following examples are provided for the purposes of illustration and are not intended to limit the scope of the present invention.

EXAMPLES

Example 1

The following example demonstrates the methods for selection of a suitable strain of the genus, Lactobacillus, for use in the present invention.

Six strains of Lactobacillus, each isolated from the vagina of six different healthy women with no history of sexually transmitted disease, were evaluated for a set of desirable characteristics. The six strains were evaluated for purity, adherence to vaginal epithelial cells, stability of genetic profile, production of hydrogen peroxide ($H_2O_2$), and stability of viability over long periods of storage. Suitable strains were selected as having purity (i.e., lack of contaminating microorganisms) as determined by the ability to maintain a substantially pure culture of the mother strain; a percent vaginal epithelial cell cohesion value of at least about 80%; a stable genetic profile as evaluated by identifying strains in which the genetic profile of the cultured cells was identical to mother strain; acceptable production of $H_2O_2$, as evaluated by formation of a pronounced blue pigment after anaerobic incubation on TMB medium, or at least about 20 ppm on an EM strip; and acceptable stability of viability, as evaluated by the ability of a medicant of the present invention to maintain between $10^7$ and $10^8$ colony forming units (CFUs) at 4–6° C. and at room temperature for at least about 12 months.

Strain CTV-05 (*Lactobacillus crispatus*) was selected as the best choice for a suppository strain based upon adherence studies, in vitro inhibition of pathogenic microorganisms, and stability of desirable strain characteristics (e.g., the ability to adhere to vaginal epithelial cells in a metabolically inactive state) in a preserved state during storage under various conditions. Cells of CTV-05 grown on MRS medium exhibit dimensions of 1–2 microns in width and 2–4 microns in length.

The following specific methods were employed to monitor the presence or absence of the desirable characteristics for a suitable Lactobacillus strain of the present invention.

(1.1) Purity of the Strain:

The purity of the suppository strain (i.e., lack of presence of contaminating organisms in a culture) was confirmed by specifically distinguishing the suppository strain from other strains using DNA fingerprinting techniques. DNA fingerprinting was performed by Repetitive Sequence Polymerase Chain Reaction (Rep PCR). In order to determine whether the Rep PCR method could distinguish the suppository strain (CTV-05) from endogenous *L. crispatus*, 40 strains of *L. crispatus* were recovered from the vagina of women of child-bearing age and compared to CTV-05. *L. crispatus* species identity was determined using whole chromosomal DNA homology to control strain *L. crispatus* ATCC 33197. All *L. crispatus* isolates had doublet bands at 4072 and 1400 base pairs, and single bands at 3500, 750, 520, 350, and 220 base pairs, suggesting that these repetitive DNA sequences are common to all strains of *L. crispatus* (data not shown). The suppository strain (CTV-05) was distinguished from the others by four bands in the 2500-1500 base pair region. In this region, the CTV-05 fingerprint consists of intense bands at 2500 and 1500 and less amplified bands at 2000 and 1736 base pairs (data not shown).

(1.2) Adherence to Vaginal Epithelial Cells (VECs):

Immediately after sampling, vaginal epithelial cells were transferred to MEM tissue culture medium, pH 7.2, washed 3 times in a syringe and passed through a $8\mu$ filter (Millipore) which retains vaginal cells but passes bacteria. A total of $10^5$ washed vaginal cells were added to a suspension of $10^9$ Lactobacilli/ml (enumerated with a counting chamber) and incubated for 2.5 hours at 37° C. After washing and filtering to remove unattached Lactobacilli, the vaginal cells were stained using Gram stain. The number of Lactobacilli that adhered to the epithelial cells was counted and recorded using a light microscope equipped with a camera. Both the mean number of Lactobacilli cells adhered per VEC (average adherence value) and the percent VEC cohesion value, as described above, were calculated. The percent VEC cohesion value, defined as the percentage of VECs to which at least one Lactobacillus cell is adhered of the total number of VECs in an identified group, was used to determine whether a particular strain would be selected as having a desirable adherence characteristic. Since ongoing adherence studies required a constant supply of vaginal epithelial cells, the vaginal epithelial cells were pre-washed and stored at -70° C. until time of use. This technique gives comparable results to freshly collected vaginal epithelial cells that have a one hour shelf-life.

Table 1 and Table 2 show the in vitro adherence studies using frozen VECs from donors representing the most prevalent ABO blood types. Table 1 shows the results of in vitro studies demonstrating adherence of actively growing cells of strain CTV-05 to VECs. Strain CTV-05 (Lot LB-022) was preserved in suppository format as described in detail in Example 3. Suppositories were stored at both room (RT) and refrigerator (Ref.) temperatures for 5.5 months prior to testing. It is important to note that the cells of strain CTV-05 used in these studies were not in an actively growing metabolic state. Rather, a suppository containing CTV-05 was placed directly into McIlvaine's buffer (pH 4.5) without pregrowing the microbial cells to an active state. The cells were then directly added to VECs. Results are shown as (1) the logarithmic mean adherence of CTV-05 per 50 VECs (X±1 standard deviation), (2) as the actual range of adhered CTV-05 per VEC in a total count of 50 VECs, and (3) as the percent VEC cohesion value (t VEC ADH). The description of terms in Table 1 is as follows: [1]X±1STD=logarithmic mean adherence of LAB per 50 VEC, ±1 standard deviation; [2] Range=actual range of adhered LAB per VEC in a total count of 50 VECs; [3] % VEC ADH=percent of 50 VECs showing adherence of LAB strain CTV-05, Lot LB-022, stored for 5.5 months at refrigerated (Ref.) and/or room temperature (RT); and *Nursing Mother.

TABLE 1

| Blood Type | | | Cycle | Culture $H_2O_2$ | | Neg. VEC | | |
|---|---|---|---|---|---|---|---|---|
| ABO | Rh | Age | Day | LAB | Measure | Control | LB-022 Ref. | LB-022 RT |
| O | Pos | 33 | 7 | Pos | X ± 1 STD[1] | 0 | 28.5 ± 2.3 | 26.5 ± 2.1 |
| | | | | | Range[2] | 0–3 | 4– > 200 | 4–103% |
| | | | | | % VEC ADH[3] | 10% | 100% | 100 |

TABLE 1-continued

| Blood Type | | | Cycle | Culture H$_2$O$_2$ | | Neg. VEC | | |
|---|---|---|---|---|---|---|---|---|
| ABO | Rh | Age | Day | LAB | Measure | Control | LB-022 Ref. | LB-022 RT |
| O | Pos | 32 | 15 | Pos | X ± 1 STD | 0 | 17.4 ± 2.9 | 18.9 ± 3.5 |
| | | | | | Range | 0 | 0–112 | 0– > 200 |
| | | | | | % VEC ADH | 0% | 94% | 98% |
| O | Pos | 38 | 20 | No growth | X ± 1 STD | 1.5 | 26.5 ± 2.1 | 27.3 ± 2.4 |
| | | | | | Range | 0–6 | 5– > 200 | 0– > 200 |
| | | | | | % VEC ADH | 16% | 100% | 98% |
| O | Neg | 23 | 17 | Pos | X ± 1 STD | 0 | 18.3 ± 2.5 | 25.0 ± 2.5 |
| | | | | | Range | 0–1 | 0–88 | 3– > 200 |
| | | | | | % VEC ADH | 2% | 98% | 100% |
| A | Neg | *26 | 8 mos | Yeast | X ± 1 STD | 0 | 27.7 ± 2.4 | 34.4 ± 2.4 |
| | | | | | Range | 0–5 | 0– > 200 | 3– > 200 |
| | | | | | % VEC ADH | 6% | 98% | 100% |
| A | Pos | 31 | 3 | Pos | X ± 1 STD | 2.9 | 30.2 ± 3.0 | 30.2 ± 3.1 |
| | | | | | Range | 0–87 | 1– > 200 | 1– > 200 |
| | | | | | % VEC ADH | 40% | 100% | 100% |
| A | Pos | 24 | 37 | Neg | X ± 1 STD | 2.4 | 20.4 ± 2.7 | 26.2 ± 2.6 |
| | | | | | Range | 0–79 | 2–125 | 3–144 |
| | | | | | % VEC ADH | 48% | 100% | 100% |
| B | Pos | 35 | 13 | No growth | X ± 1 STD | 3.4 | 5.8 ± 3.5 | 6.1 ±6.1 |
| | | | | | Range | 0–28 | 0–65 | 0–184 |
| | | | | | % VEC ADH | 16% | 86% | 84% |
| | | | | | Overall AVG's | | | |
| | | | | | #LAB/VEC | 1.3 | 21.9 | 24.3 |
| | | | | | % VEC/ADH | 17.3% | 97% | 97.75% |

The average adherence value for room temperature stored cells of strain CTV-05 for the 8 VEC donors was 21.9 cells/VEC. The average adherence value for cells of strain CTV-05 stored at refrigerated temperatures for the 8 VEC donors was 24.3 cells/VEC. Adherence ranges for individual VEC donors were quite wide (i.e., 0 to more than 200 cells of CTV-05 per VEC). However, the percentage of VECs showing adherence of at least one cell of the suppository strain (percent VEC cohesion value) averaged 97% for CTV-05 stored at room temperature and 97.75% for CTV-05 stored at refrigerated temperature, respectively.

These results suggest that cells of strain CTV-05 are more likely to colonize human VECs in vivo since they are able to immediately adhere to VECs in vitro after release from the suppository while still in a metabolically inactive state. Once the preserved cells are adhered to VECs, it can be predicted that they revive and proliferate (i.e., colonize) instead of being shed from the vaginal milieu.

Table 2 shows the results from studies in which inactive CTV-05 from either broth or agar cultures was added directly to VECs in McIlvaines Buffer (pH 4.5). The buffer was then added directly to previously frozen VECs from human donors. Actively growing CTV-05 was also added to previously frozen VECs. Table 2 shows the same parameters as described above for Table 1. The results shown in Table 2 demonstrate that inactive CTV-05 (i.e., from a preserved state) adhere to VECs equally well or better than CTV-05 added to VECs in a metabolically active state.

TABLE 2

| Donor information | | | | | | Frozen VECs, McIlvaines Buffer pH 4.5 | | | |
|---|---|---|---|---|---|---|---|---|---|
| | | | | | | Neg VEC | | Inactive LAB | |
| Blood Type | Age | Race | Cycle Day | Gram Stain Score | Measure | Control | Active LAB | Agar | Broth |
| A+ | 25 | C | 17 | 9 | X ± 1STD | NA | 13.0 ± 5.0 | ND | 3.1 ± 3.2 |
| | | | | | Range | 0–1 | 0– > 200 | | 0– > 200 |
| | | | | | % VEC ADH | 1% | 66% | | 38% |
| B+ | 35 | C | 13 | 9 | X ± 1STD | NA | 5.7 ± 3.3 | 19.4 ± 3.9 | 7.3 ± 4.7 |
| | | | | | Range | 0–5 | 0–61 | 1– > 200 | 0– > 200 |
| | | | | | % VEC ADH | 16% | 68% | 100% | 60% |
| A+ | 24 | C | 37 | 8 | X ± 1STD | NA | 8.5 ± 3.3 | 58.9 ± 2.1 | 10.9 ± 3.6 |
| | | | | | Range | 0–5 | 0–133 | 7– > 200 | 0– > 200 |
| | | | | | % VEC ADH | 24% | 94% | 100% | 98% |
| O+ | 38 | C | 20 | 6 | X ± 1STD | NA | 14.1 ± 2.3 | 60.9 ± 2.1 | 15.9 ± 3.1 |
| | | | | | Range | 0 | 1–122 | 11– > 200 | 1–66 |
| | | | | | % VEC ADH | 0% | 100% | 200% | 100% |
| A– | 26 | C | 8 mos. | 4 | X ± 1STD | NA | 52.1 ± 3.6 | ND | 6.5 ± 3.0 |
| | | | | | Range | 0–3 | 0– > 200 | | 0–56 |
| | | | | | % VEC ADH | 10% | 96% | | 99% |
| O+ | 22 | C | 7 | 4 | X ± 1STD | NA | 36.3 ± 2.7 | ND | 7.8 ± 3.1 |
| | | | | | Range | 0–16 | 0– > 200 | | 0–96 |
| | | | | | % VEC ADH | 48% | 92% | | 92% |

TABLE 2-continued

| Donor information | | | | | Frozen VECs, McIlvaines Buffer pH 4.5 | | | |
| --- | --- | --- | --- | --- | --- | --- | --- | --- |
| | | | | | Neg VEC | | Inactive LAB | |
| Blood Type | Age | Race | Cycle Day | Gram Stain Score | Measure | Control | Active LAB | Agar | Broth |
| A+ | 31 | C | 3 | 4 | X ± 1STD | NA | 17.7 ± 3.2 | 96.1 ± 2.3 | 6.4 ± 3.9 |
| | | | | | Range | 0–3 | 0– > 200 | 14–200 | 0– >200 |
| | | | | | % VEC ADH | 6% | 94% | 0– > 200 | 46% |
| AB+ | 39 | B | 24 | 4 | X ± 1STD | NA | 5.1 ± 3.4 | 47.3 ± 2.5 | 7.1 ± 3.5 |
| | | | | | Range | 0–3 | 0–109 | 2– > 200 | 0–178 |
| | | | | | % VEC ADH | 6% | 70% | 100% | 72% |
| O+ | 33 | C | 7 | 2 | X ± 1STD | NA | 51.9 ± 3.0 | 21.4 ± 2.5 | 5.7 ± 2.8 |
| | | | | | Range | 0–5 | 0– > 200 | 1– > 200 | 1–96 |
| | | | | | % VEC ADH | 14% | 94% | 100% | 100% |
| O+ | 32 | C | 15 | 2 | X ± 1STD | NA | 16.4 ± 4.0 | 1.9 ± 2.1 | 6.9 ± 3.3 |
| | | | | | Range | 0–5 | 0–216 | 0–11 | 1– > 200 |
| | | | | | % VEC ADH | 8% | 96% | 38% | 80% |
| | | | | Overall | # LAB/NEC | | 22.1 | 43.7 | 7.76 |
| | | | | Averages | % Adherence | | 77.6 | 91.1 | 78.4 |

(1.3) Stability of Genetic Profiles:

Genetic marker profiles based on restriction endonuclease patterns were performed at appropriate times to establish stability of genetic profiles after preservation, to confirm colonization of the suppository strain during in vivo human trials and to serve as a means of strain identity in commercial preparations. Lactobacilli were grown to mid log phase in heart infusion broth supplemented with glucose, starch and 1% serum. DNA was extracted using a 10 mm Tris buffer with 50 mM EDTA with Mutanolysin (Miles Laboratories, Naperville, Ill.) and lysozyme, a lysine solution which has been demonstrated to be effective for Lactobacillus acidophilus. Three restriction endonucleases were used for each isolate: HindIII, BamHI and EcoR1 (Bethesda Research Laboratories, Inc., Gaithersburg, Md.). The DNA fragments were electrophoresed in a 0.7% agarose gel (Seakem-ME; FMS Corp., Marine Colloids Division, Rockland, Me.) at 25V for 15 hours in Tris borate buffer (pH 8.3). The gels were stained with 1 $\mu$g/ml of ethidium bromide for 30 minutes. DNA fragments were visualized with shortwave UV and photographed. The degree of restriction endonuclease similarity between the DNA fingerprints was calculated by the following formula: degree of similarity=100%−(Nd×100)/Ns, where Ns is the sum of the bands of the 2 DNA fingerprints to be compared and Nd represents the number of bands found in only one fingerprint. A DNA probe was developed to detect a strain-specific marker which was used to identify the suppository stain. DNA homology studies were also performed to confirm the presence of the suppository strain at any given point.

(1.4) Production of $H_2O_2$:

Strains were inoculated onto tetramethylbenzidine medium (TMB) and incubated at 37° C. for 2–3 days under anaerobic conditions. $H_2O_2$-producing colonies produce a blue pigment upon exposure to ambient air. Alternatively, $H_2O_2$-detecting strips from EM Science were used. The reagent impregnated portion of the strip was applied to a Lactobacillus colony and the intensity of the resulting blue color served as a quantitative measure of $H_2O_2$ concentration.

(1.5) Stability of Viability:

Samples of each evaluated strain were retained for shelf-life studies at room temperature and refrigerated storage. At selected time intervals, samples were tested for the number of colony-forming-units using the Plate Count method with MRS agar.

Figure 2:
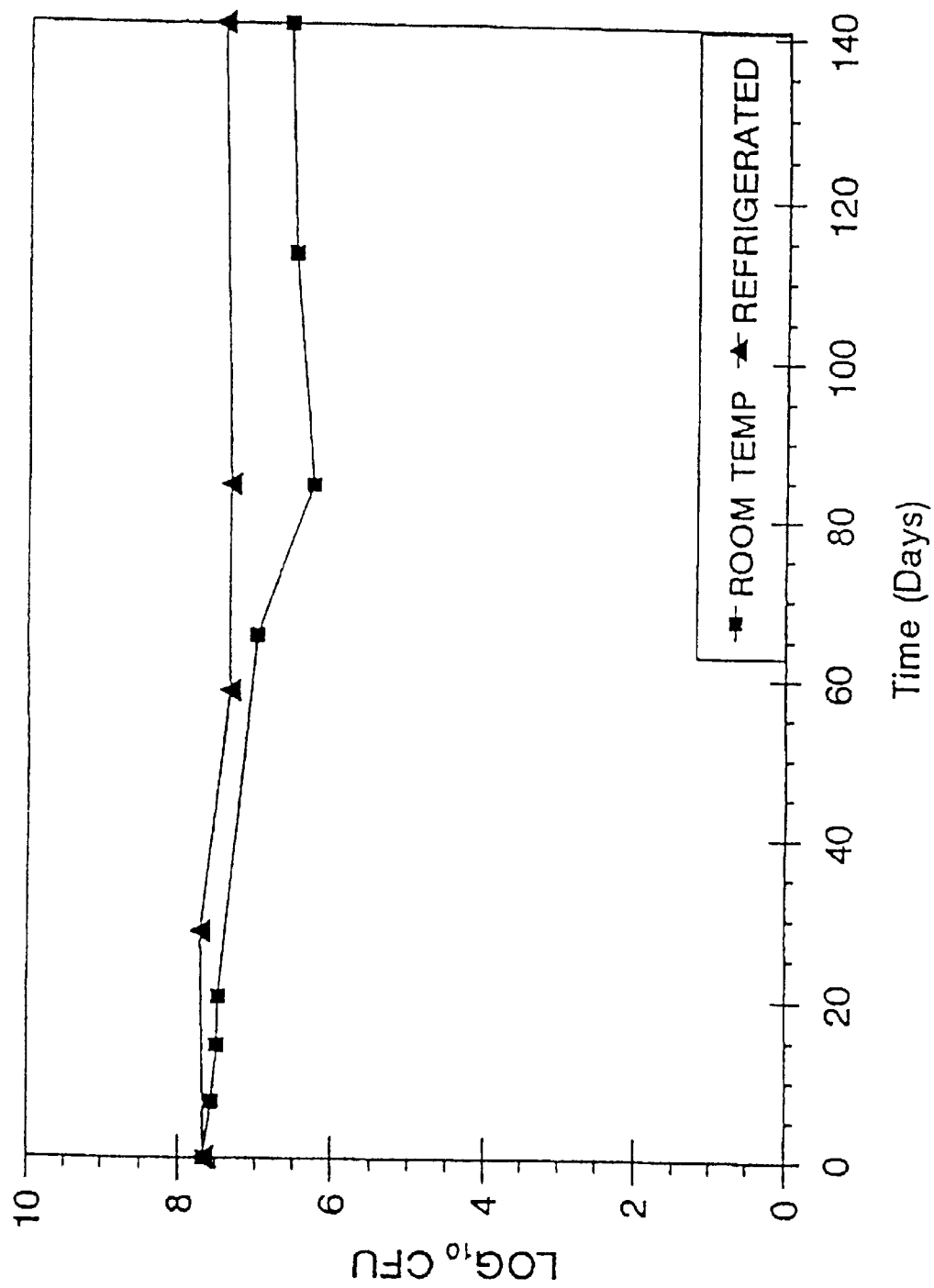
FIG. 2 is a graph showing the effect of long-term room temperature and refrigerated storage on the stability of viability of Lactobacillus strain CTV-05.

Strain CTV-05 was tested in a gelatin capsule suppository during storage at 55° C., 45° C., 35° C. and at room and refrigeration temperatures. This study was performed as a model of accelerated shelf-life storage and to demonstrate stability during adverse conditions which may occur when a commercial product is shipped throughout a global distribution network. FIG. 1 shows the results of the elevated temperature testing and FIG. 2 provides longer term results at lower temperatures. Refrigerated product colony counts have remained stable at $10^8$ per suppository for 5 months with no loss of desirable characteristics. Colony counts of product stored at room temperature remained stable at $10^8$ per suppository for 4 weeks. Between the fourth and ninth weeks counts dropped to $9.8 \times 10^7$ per suppository and have remained at $10^7$ for 25 months. $H_2O_2$ production also remained stable during this time period.

The effect of the preservation matrix on microbial survival was evaluated at pH values in a range of 4.0–7.0 (data not shown). This represents the range of pH observed in normal women (4.0–4.5), women with bacterial vaginosis (pH 5.0–6.0) and menstruating women (pH 7.0). Survival of the microbes was acceptable throughout the pH range, with pH 7.0 being optimal.

Example 2

The following example shows the determination of the optimal cell to preservation matrix ratio for providing high viability counts of preserved strain CTV-05 cells.

Experiments were conducted to determine the preservative capacity of the suspending medium by addition of different amounts of cells of strain CTV-05 per volume of medium. The Lactobacilli were grown anaerobically on 2 inch squares on MRS agar plates. A 2-inch square of agar is the equivalent of 10 ml of broth. The anticipated yield per plate was $2 \times 10^9$ CFUs. Inoculated matrix was preserved in aliquots of 30 microliters. Table 3 shows that the best results were obtained with 48 hour old strain CTV-05 cells in an 8 plate/5 ml matrix ratio. The data further demonstrates that an optimal cell to preservation matrix ratio has been achieved for providing high viability counts of preserved strain CTV-05 cells.

TABLE 3

| No. of Plates | Estimated yield/30 µl | 24 hr. Growth Period | | 48 hr. Growth Period | |
|---|---|---|---|---|---|
| | | Pre-dry | Post-dry | Pre-dry | Post-dry |
| 4 | $5.3 \times 10^7$ | $7.9 \times 10^7$ | $1.1 \times 10^7$ | $6.0 \times 10^8$ | $6.1 \times 10^8$ |
| 6 | $7.9 \times 10^7$ | $1.9 \times 10^8$ | $2.1 \times 10^7$ | $7.8 \times 10^8$ | $3.0 \times 10^8$ |
| 8 | $1.1 \times 10^8$ | $6.9 \times 10^7$ | $3.6 \times 10^7$ | $9.8 \times 10^8$ | $4.3 \times 10^8$ |
| 10 | $1.3 \times 10^8$ | $6.7 \times 10^7$ | $4.0 \times 10^7$ | $1.5 \times 10^9$ | $4.1 \times 10^8$ |

Example 3

The following example describes a particular method for preparation of a vaginal medicant of the present invention.

MRS medium used in all of the experiments described herein is composed as follows: A medium containing 10 g Bacto Proteose Peptone No. 3, 10 g Bacto Beef Extract, 5 g Bacto Yeast Extract, 20 g Bacto Dextrose Extract, 1 g Tween 80, 2 g ammonium citrate, 5 g sodium acetate, 0.1 g magnesium sulfate, 0.05 g manganese sulfate, and 2 g dipotassium phosphate was brought up to 1000 ml with reagent grade $H_2O$. For MRS agar, 10 g of agar was added to the mixture. The medium was adjusted to pH 6.5±0.2 at 25° C.

Preservation matrix can be prepared as follows. 2× gelatin (e.g., 137.5 g per 500 ml reagent water) and 4× skim milk (e.g., 15 g per 250 ml reagent water) is autoclaved at about 121° C. for about 15 minutes. 4× xylitol (e.g., 59 g per 250 ml reagent water) and 4× dextrose (e.g., 25 g per 250 ml reagent water) are mixed together, adjusted to pH 7.2–7.4 and filter sterilized with a 0.22 micron filter. The sterile components are then combined into a single solution (gelatin base) and stored at 2–8° C. Ascorbic acid is prepared as a 5% by weight solution, filter sterilized with a 0.22 micron filter, dispensed into aliquots of suitable volumes for production, and stored at −20° C. At the time of production of a vaginal medicant, the gelatin base is melted and tempered to about 35° C. and the 5% ascorbic acid is added to the gelatin base at a ratio of 1:10 to form the preservation matrix.

To produce the vaginal medicant, MRS medium is inoculated with about $10^6$ to about $10^9$ CFUs/ml culture of a Lactobacillus strain. The inoculum is cultured at between 20° C. to 35° C. anaerobically or microaerophilically until the culture reaches a cell density of from about $10^7$ to about $10^9$ CFUs/ml of culture.

The cells are harvested by centrifugation for 5 minutes at 1400–1600 rpm. The supernatant is decanted into a waste container, or can be salvaged for other by products. The cell pellets are resuspended in a phosphate buffer saline (PBS) and centrifuged again for 5 minutes at 1400–1600 rpm. The supernatant from this wash step is discarded. The packed cells are then resuspended in 1 part phosphate buffer and 10 parts preservation matrix. The cell matrix suspension is mixed gently and thoroughly and maintained at 35° C. +5° C. with continuous mixing.

To form the complete vaginal medicant, a fluid bed dryer having sterilized components is assembled for use. Maltodextrin beads are placed into the fluid bed dryer and are dried at 33° C. until sufficiently dry. The air pressure is then set to 14 psi, and the cell suspension matrix is sprayed onto the beads using a peristaltic pump. After 50% of the cell matrix suspension is sprayed onto the maltodextrin beads, the heat is increased to 38° C. After all of the cell matrix suspension has been sprayed onto the beads, the coated beads are then allowed to dry at about 38° C. for about 15–30 additional minutes. The coated maltodextrin beads can be frozen, stored as a powder, placed into gelatin capsules, or pressed into tablets for use as a vaginal medicant.

Example 4

The following example illustrates the effectiveness of Rep PCR for evaluating different lots of an L. crispatus suppository.

Six different lots of L. crispatus CTV-05 prepared over a 2 year period were evaluated for purity and stability of the genetic fingerprint. All of the lots evaluated were free of contaminants when incubated in an enriched chopped meat broth incubated anaerobically. In addition, the various lots of L. crispatus prepared under small scale and scale-up lots had identical fingerprints (data not shown). These data suggest that the L. crispatus CTV-05 suppository retains viability, purity and genetic stability over years of storage. Further, there has been no lot-to-lot variability in the "fingerprint" of the DNA of the suppository strain (data not shown).

Example 5

The following example demonstrates that the Lactobacilli of the present invention can be used in vivo in a suppository to recolonize the vagina of normal, healthy women with Lactobacilli.

In this open study, a Lactobacillus suppository containing approximately $10^9$ viable, $H_2O_2$-producing Lactobacillus crispatus CTV-05 was used by 9 women twice daily for three days. All 9 women were free of genital infection at enrollment, and 8 of the 9 women had endogenous Lactobacilli at enrollment. At follow-up 2–3 days after use of the last suppository capsule, all of the women were colonized by the suppository strain, and 8 of 9 women remained colonized at 1 month. None of the women had evidence of inflammation microscopically (e.g., by evaluation of white blood cells on the vaginal smear), and none complained of side effects.

Since many women are colonized vaginally and rectally by Lactobacilli, the technique, Repetitive Sequence Polymerase Chain Reaction (Rep PCR), was used to "fingerprint" the suppository strain of L. crispatus and thereby distinguish the suppository strain from endogenous strains of Lactobacilli. Fingerprinting results from the first clinical pilot study demonstrated that the L. crispatus CTV-05 suppository's genetic fingerprint is preserved over several months of vaginal colonization.

Patient 102 was colonized by a non-crispatus Lactobacillus at enrollment. At the one week visit after use of the suppository she was colonized by three strains of Lactobacilli, which included (1) the suppository strain, L. crispatus CTV-05; (2) the same strain with which she had been colonized at enrollment; and (3) a new strain of Lactobacilli which was not CTV-05 and which was not present at enrollment (data not shown). At the one month visit, the patient was still colonized by *L. crispatus* CTV-05, as well as by the strain of Lactobacilli present at the first follow-up and the strain present at enrollment (data not shown). The subject was evaluated one year after enrollment and it was found that she was colonized exclusively by the suppository strain, *L. crispatus* CTV-05. These studies demonstrate the present inventor's ability to "fingerprint" the suppository strain of *L. crispatus* CTV-05 and demonstrate that this genetic fingerprint is preserved in vivo over several months of vaginal colonization.

Patient 103 was colonized by Lactobacilli at enrollment but not by *L. crispatus*. One week after use of the CTV-05 suppository twice daily for 3 days, she was colonized by CTV-05 as well as by another strain of Lactobacilli (data not shown). Four weeks later, this women was still colonized with CTV-05 as well as with the strain of Lactobacillus which she carried at the first follow-up visit (data not shown).

Example 6

The following example is an in vivo study which demonstrates that the Lactobacilli of the present invention can be used in vivo in a suppository to recolonize the vagina of women having recurrent vaginosis.

In this study, a group of women with recurrent bacterial vaginosis (BV) was treated with 2% Clindamycin cream, once daily for three days, followed by Lactobacillus suppositories containing the *Lactobacillus crispatus* CTV-05 strain twice daily for three days. A group of women from the same clinic with recurrent bacterial vaginosis treated with Clindamycin cream alone were included for comparison. Women were seen for follow-up at one week after completion of therapy, at one month, and at 3–4 months after enrollment. The patients were evaluated for vaginal presence of $H_2O_2$-producing Lactobacilli, and the absence of bacterial vaginosis infection.

The results from this study are shown in Table 4. Table 4 shows that, of the women that had recurrent bacterial vaginosis, the group which was treated with both the Clindamycin cream and the *Lactobacillus crispatus* CTV-05 suppository, a significantly higher percentage of the women were colonized with $H_2O_2$-producing Lactobacilli at each stage of post-treatment evaluation compared to the women who received Clindamycin cream only.

TABLE 4

| | Percentage Women Colonized with $H_2O_2$-producing Lactobacilli | |
|---|---|---|
| Time of Evaluation | Clindamycin Only n = 15 | Clindamycin plus Lactobacillus Suppository n = 15 |
| Enrollment | 5 (33%) | 4 (27%) |
| One week post treatment | 1 (7%) | 10 (67%) |
| One month post treatment | 6 (40%) | 12 (80%) |
| Three months post treatment | 5 (33%) | 10 (67%) |

In order to ascertain whether the peroxide-producing Lactobacilli present were attributable to the suppository, the DNA from these Lactobacilli was hybridized under high stringency with the purified DNA from the suppository strain. In addition, each isolate was fingerprinted based on detection of preformed enzymes detected using 4-methylumbelliferyl substrates. In the group of women receiving Clindamycin only, none of the women acquired a Lactobacillus strain which was identical to the suppository. In contrast, all of the women who were treated with Clindamycin plus the Lactobacillus suppository, and who were colonized with a Lactobacillus strain after treatment, had the suppository strain.

Table 5 shows that, of the women who received Clindamycin plus the *Lactobacillus crispatus* CTV-05 suppository, 100% of the women were free of bacterial vaginosis at one month after treatment, as compared to only 53% of the women who received Clindamycin alone. Similarly, at three months after treatment, 54% of the women who received Clindamycin plus the Lactobacillus suppository were free of bacterial vaginosis as compared to only 26% of the women who received Clindamycin alone. This data suggests that the *Lactobacillus crispatus* CTV-05 suppository of the present invention may decrease the recurrence of bacterial vaginosis.

TABLE 5

| | Percentage Women Free of Bacterial Vaginosis | |
|---|---|---|
| Time of Evaluation | Clindamycin Only | Clindamycin plus Lactobacillus Suppository |
| One week post treatment | 13/15 (87%) | 15/15 (100%) |
| One month post treatment | 8/15 (53%) | 13/13 (100%) |
| Three months post treatment | 4/15 (26%) | 7/13 (54%) |

Example 7

The following example is an in vivo study which demonstrates that the Lactobacilli of the present invention can be used in vivo in a suppository to recolonize the vagina of women who have bacterial vaginosis.

In this study, 13 women who had bacterial vaginosis were given *Lactobacillus crispatus* CTV-05 suppositories twice daily for seven days. The purpose of this study was to evaluate whether Lactobacillus suppositories could be used as a treatment for bacterial vaginosis. Only 1 of 10 women who returned for follow-up was cured of bacterial vaginosis at the one week follow-up visit. Lactobacillus cultures performed at baseline and at follow-up, however, showed that 7 of the 10 women with bacterial vaginosis were successfully colonized by the suppository strain (data not shown). None of the women experienced any side-effects from use of the *Lactobacillus crispatus* CTV-05 suppositories, and none had either visual or microscopic evidence of inflammation.

The studies presented in Examples 5 6, and 7 have shown that the Lactobacilli of the present invention can be used in a suppository to recolonize the vagina with Lactobacilli. Over fifty women have been included in clinical trials with the *Lactobacillus crispatus* CTV-05 suppository. None of the women who received the suppository had any side effects associated with its use. These pilot data further demonstrate that *Lactobacillus crispatus* having the preferred characteristics of strain CTV-05, applied in the form of a gelatin capsule inserted into the vagina, 1) will successfully colonize the vagina of women with normal vaginal flora with greater than 80% remaining colonized after one month; 2) can colonize women with active bacterial vaginosis; 3) can colonize women with bacterial vaginosis following treatment and 4) may result in decreased recurrence of bacterial vaginosis following treatment (as shown by the decreased recurrence of bacterial vaginosis following treatment in 100% of the individuals in Example 5 at one month following treatment). Furthermore, the present inventors have developed fingerprinting methods which allow the identification of the suppository strain of *L. crispatus* in human trials.

Example 8

This example demonstrates that the preservation matrix of the present invention is superior to the industry standard skim milk matrix in maintaining viability of microorganisms during the preservation process as well as during storage.

Lyophilization (e.g., freeze-drying) has historically been the accepted method of choice for long term preservation of microorganisms. Skim milk is one of the standard cryopreservation matrices used by the American Type Culture Collection and is frequently used by the dairy industry. In the following experiments, the present inventors demonstrate that the preservation matrix of the present invention outperforms this skim milk industry standard as determined by several parameters.

Cells of *Lactobacillus crispatus* CTV-05 were grown by inoculating 500 ml of MRS broth with 5 ml of a suspension cells which had been grown for 24 hours on MRS agar that was incubated at 35° C. under anaerobic conditions. After incubation of the inoculated broth for 48 hours at 35° C. under anaerobic conditions, the broth was centrifuged to concentrate the lactobacilli.

The total cell yield from 500 ml of broth was combined with either 50 ml of the preservation matrix of the present invention or with 50 ml of 10% skim milk to form suspensions. Each suspension was then divided into equal halves. One half of each suspension was dispensed for air drying using silica gel as a desiccant (LB107 preservation matrix and LB109=skim milk), and the remaining one half of each suspension was dispensed for freeze drying (LB106= preservation matrix and LB108=freeze drying).

Pre- and post-preservation colony forming unit (CFU) counts were performed by suspending and/or rehydrating the product in MRS broth and then preparing 10-fold dilutions in MRS broth. Spread plates of 3 consecutive dilutions were prepared on MRS agar and incubated for 48 hours under anaerobic conditions at 35° C.

As shown in Table 6, no significant loss of viability occurred during either type of preservation process when the microorganisms were preserved in a preservation matrix of the present invention, however, microorganisms preserved in the industry standard skim milk lost one log of viability during both preservation processes.

TABLE 6

| | | | CFU | |
|---|---|---|---|---|
| Lot No. | Matrix | Method | Pre-preservation | Post-preservation |
| LB-106 | Preservation matrix | Freeze Dried | 9.5 E+08 | 5.4 E+08 |
| LB-107 | Preservation matrix | Air Dried | 9.5 E+08 | 8.4 E+08 |
| LB-108 | Skim milk | Freeze Dried | 5.8 E+08 | 7.9 E+07 |
| LB-109 | Skim milk | Air Dried | 5.8 E+08 | 2.8 E+07 |

An accelerated shelf-life study was performed by storing aliquots of each of the above-referenced lots at 35° C. and at 44.5° C. At 6 hour intervals, CFU determinations were performed as previously described. Results are presented in FIGS. 8 through 11. The actual CFUs are shown in Table 7. Data were log transformed for the preparation of the figures.

TABLE 7

| Composition | Temp. | CFUs Over Time (Hours) | | | | | | | | |
|---|---|---|---|---|---|---|---|---|---|---|
| | | 0 | 6 | 12 | 18 | 24 | 30 | 36 | 42 | 48 |
| Preservation Matrix Air Dried LB-107 | 35° C. | 8.40E + 08 | 8.10E + 08 | 5.60E + 08 | 4.10E + 07 | 2.80E + 08 | 3.00E + 08 | 2.40E + 08 | 2.60E + 08 | 5.70E + 08 |
| | 44.5° C. | 8.40E + 08 | 3.50E + 08 | 1.80E + 08 | 8.60E + 05 | 2.30E + 07 | 6.40E + 05 | 6.80E + 05 | 1.30E + 06 | 7.10E + 08 |
| Skim Milk Air Dried LB-109 | 35° C. | 2.80E + 07 | 4.10E + 06 | 2.60E + 06 | 8.80E + 04 | 1.40E + 08 | 3.30E + 06 | 1.30E + 05 | 1.70E + 05 | 3.70E + 05 |
| | 44.5° C. | 2.80E + 07 | 3.10E + 05 | 8.20E + 04 | 3.70E + 04 | 1.00E + 01 | 1.00E + 01 | 3.10E + 03 | 3.00E + 03 | 1.00E + 01 |
| Preservation Matrix Freeze Dried LB-106 | 35° C. | 5.40E + 08 | 3.00E + 08 | 2.40E + 08 | 1.10E + 08 | 8.80E + 07 | 5.90E + 07 | 1.90E + 08 | 3.10E + 07 | 1.30E + 07 |
| | 44.5° C. | 5.40E + 08 | 1.10E + 08 | 5.80E + 07 | 1.00E + 01 | 1.00E + 01 | 1.00E + 01 | 1.00E + 01 | 1.00E + 01 | 1.00E + 01 |
| Skim Milk Freeze Dried LB-108 | 35° C. | 7.90E + 07 | 1.80E + 06 | 6.70E + 05 | 7.40E + 05 | 1.10E + 05 | 7.10E + 04 | 5.00E + 04 | 4.20E + 04 | 1.50E + 03 |
| | 44.5° C. | 7.90E + 07 | 4.50E + 06 | 9.00E + 04 | 1.00E + 03 | 1.00E + 01 | 1.00E + 03 | 1.00E + 03 | 1.00E + 01 | 1.00E + 01 |

Figure 3:
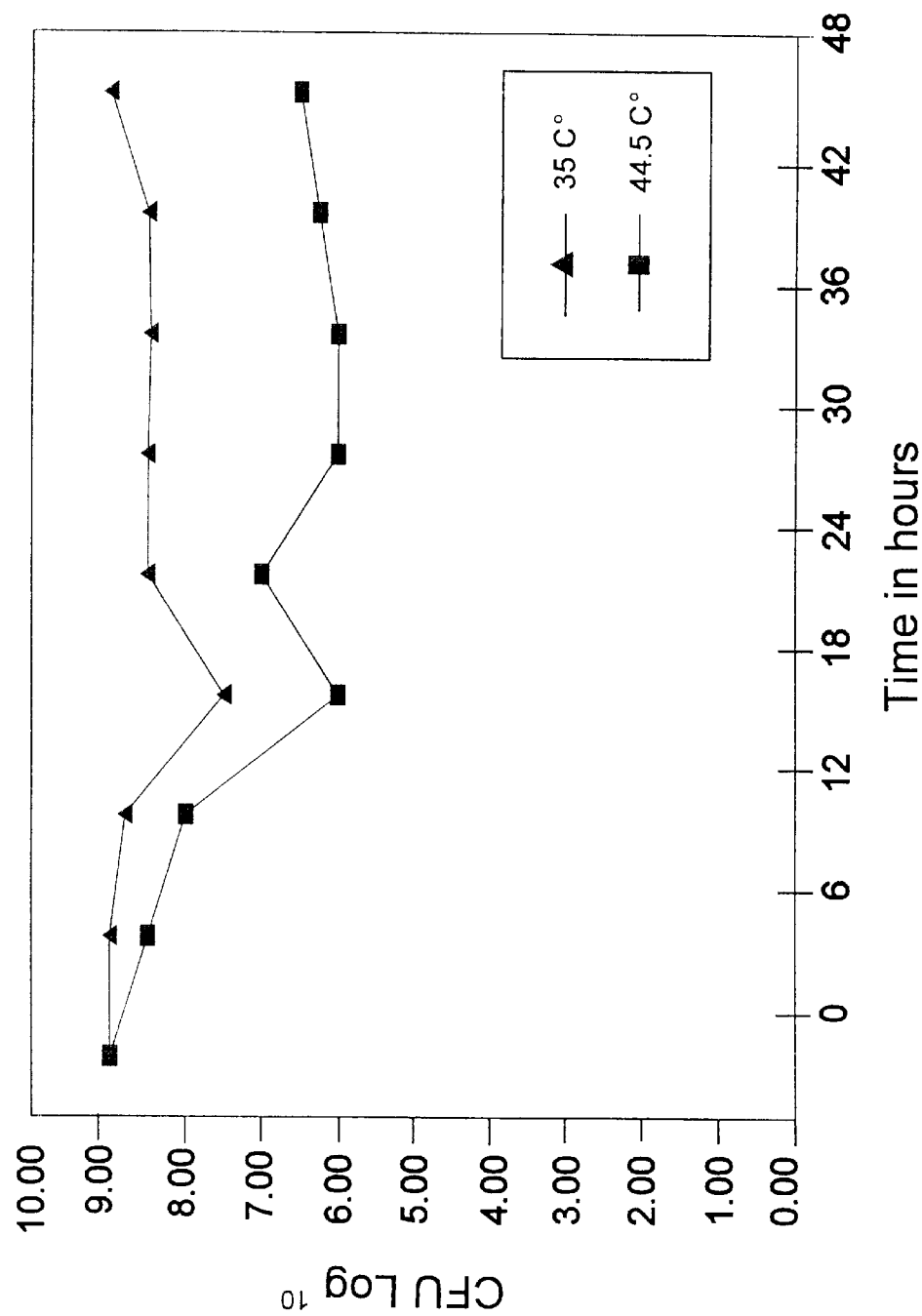
FIG. 3 is a line graph of an accelerated shelf-life study showing the viability over time of *Lactobacillus crispatus* CTV-05 preserved in an air-dried preservation matrix of the present invention.

FIG. 3 shows the results for the air-dried cell/preservation matrix suspension of the present invention, Lot LB-107. This lot showed no loss of viability during the preservation process and showed no loss of viability when stored at 35° C. for 48 hours, but did loose 2 logs of viability during storage for 48 hours at 44.5° C.

This experiment also shows that the cell/preservation matrix suspension of the present invention which was coated onto maltodextrin by the fluid drying process gave the most stable product when stored at either 35° C. or 44.5° C. when compared to the air-dried or freeze-dried suspending matrices studied in Example 8 above.

TABLE 8

Preservation Matrix - Fluid Bed Dried on Maltodextrin LB-096

| | CFUs Over Time (Hours) | | | | | | | | |
|---|---|---|---|---|---|---|---|---|---|
| Temp. | 0.00 | 6 | 12 | 18 | 24 | 30 | 36 | 42 | 48 |
| 35° C. | 1.60E + 08 | 2.00E + 08 | 9.00E + 07 | 1.70E + 08 | 3.00E + 09 | 1.10E + 08 | 2.00E + 08 | 2.00E + 08 | 1.30E + 08 |
| 44.5° C. | 1.60E + 08 | 1.40E + 08 | 1.20E + 08 | 1.20E + 08 | 4.10E + 07 | 9.60E + 07 | 1.10E + 08 | 4.40E + 07 | 6.60E + 06 |

Figure 4:
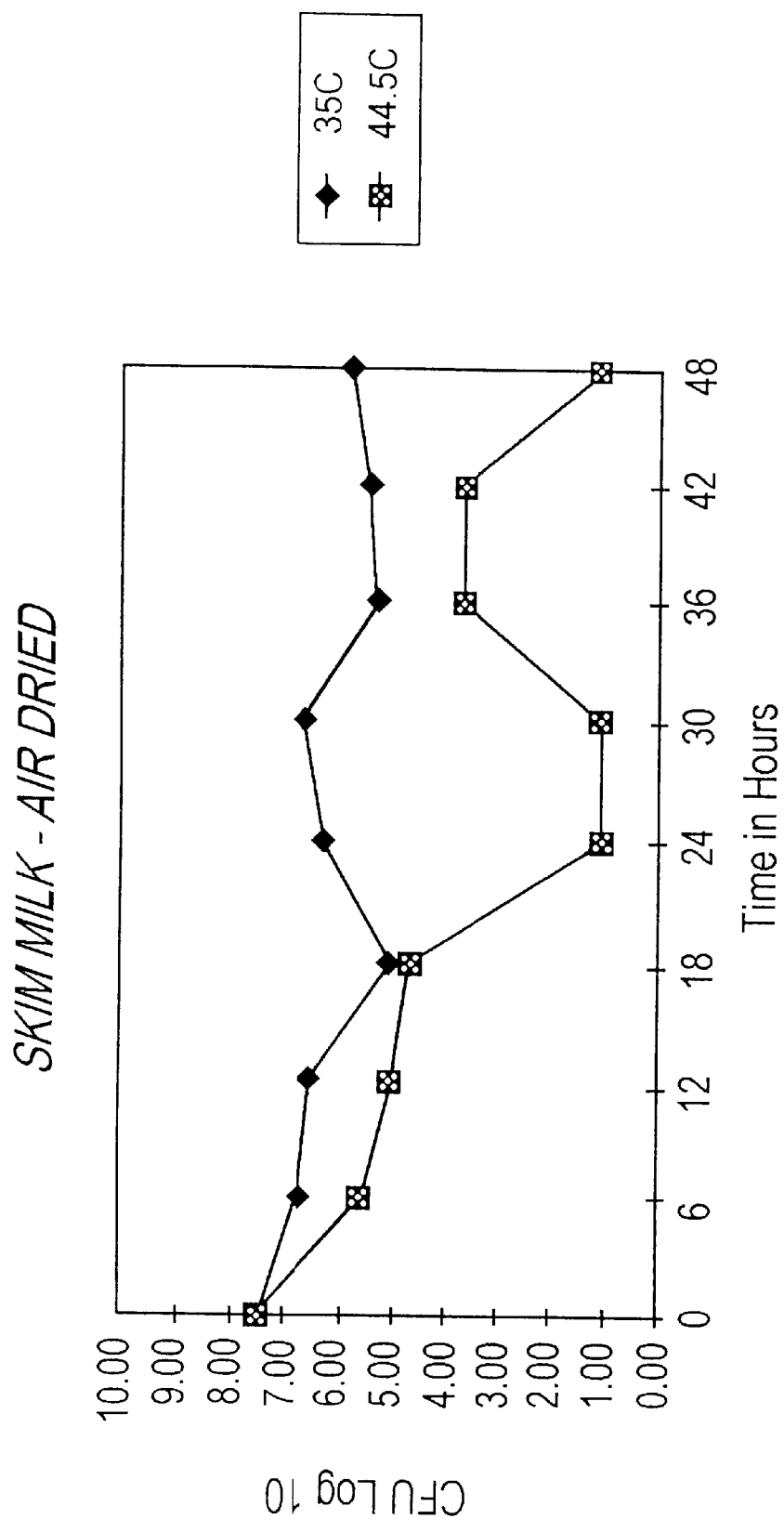
FIG. 4 is a line graph of an accelerated shelf-life study showing the viability over time of *Lactobacillus crispatus* CTV-05 preserved in an air-dried, standard skim milk matrix.

FIG. 4 shows the results for the air-dried cell/skim milk suspension, Lot LB-109. This lot lost 1 log of viability during the preservation process and lost 2 more logs of viability by 48 hours at 35° C. The product stored at 44.5° C. lost substantially all viability by 24–48 hours.

Figure 5:
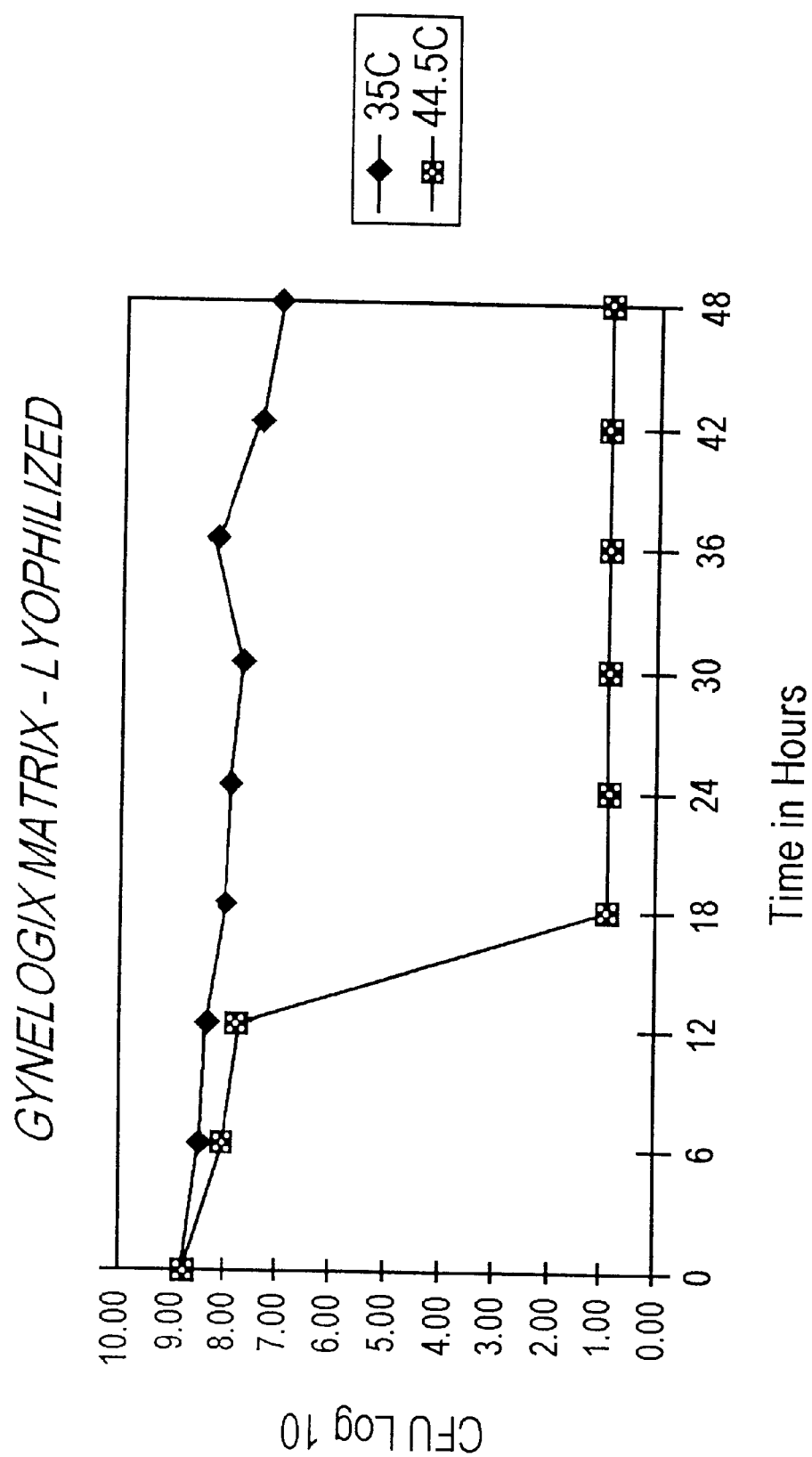
FIG. 5 is a line graph of an accelerated shelf-life study showing the viability over time of *Lactobacillus crispatus* CTV-05 preserved in an freeze-dried preservation matrix of the present invention.

FIG. 5 shows the results for the freeze-dried cell/preservation matrix suspension of the present invention, Lot LB-106. This lot showed no loss of viability during the preservation process and showed no loss of viability in 18 hours at 35° C., but lost 1 log of viability by 48 hours at 35° C. The product stored at 44.5° C. lost substantially all viability within 18 hours.

Figure 6:
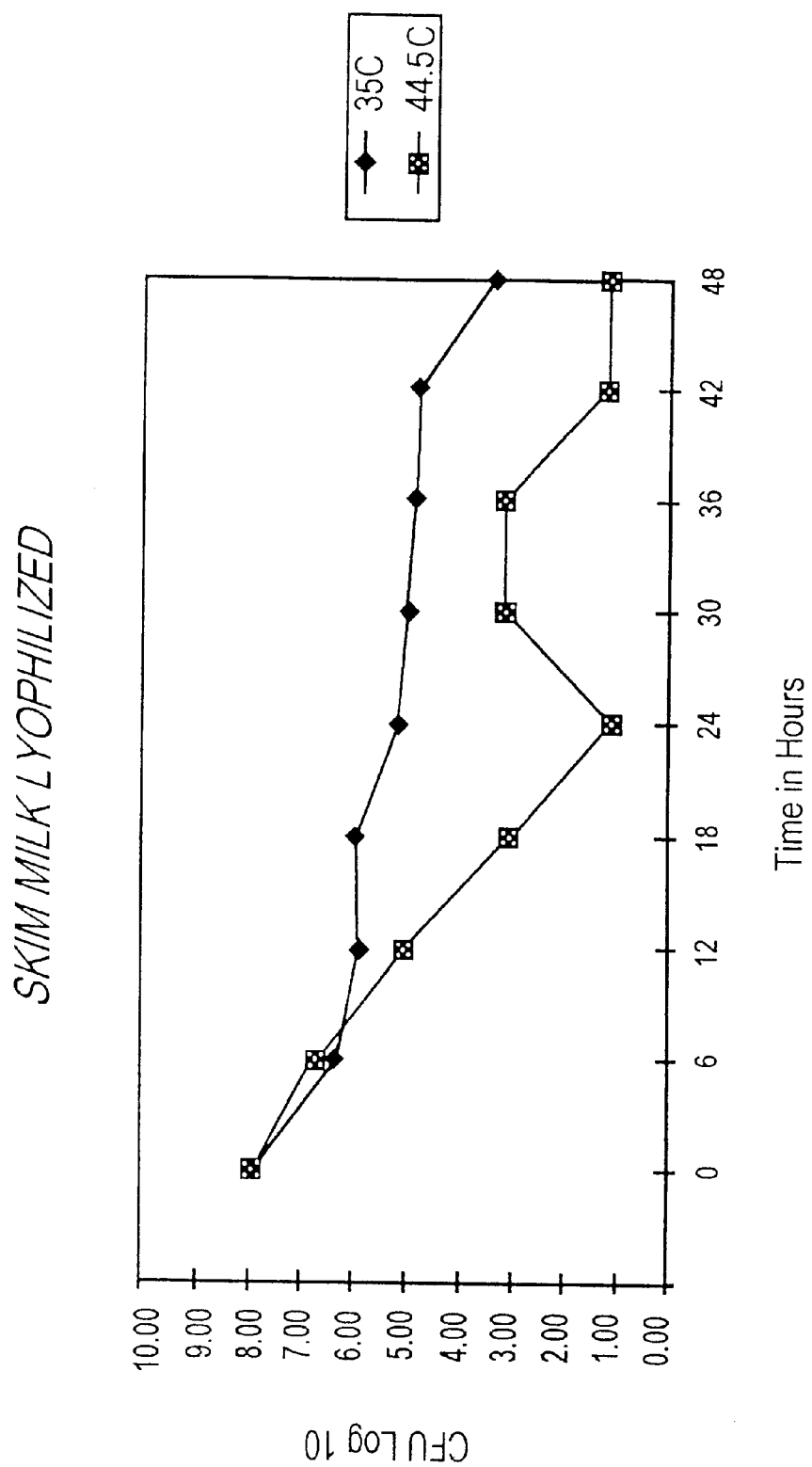
FIG. 6 is a line graph of an accelerated shelf-life study showing the viability over time of *Lactobacillus crispatus* CTV-05 preserved in an freeze-dried, standard skim milk matrix.

FIG. 6 shows the results for the freeze-dried cell/skim milk suspension, Lot LB-108. This lot lost 1 log of viability during the preservation process and lost 4 more logs of viability by 48 hours at 35° C. The product stored at 44.5° C. lost substantially all viability by 24–48 hours.

In summary, the lots prepared using the preservation matrix of the present invention out-performed the industry standard skim milk lots during the preservation process by either air drying or by freeze drying. The viability during storage for either preservation matrix lots was also superior to either of the skim milk lots, demonstrating that the preservation matrix of the present invention is superior to the industry standard skim milk matrix.

Example 9

The following example shows accelerated and real time storage experiments which demonstrate that cells preserved using a preservation matrix of the present invention are stable over time in both refrigerated and room temperature storage conditions. This example also demonstrates the versatility of the preservation matrix of the present invention.

Figure 7:
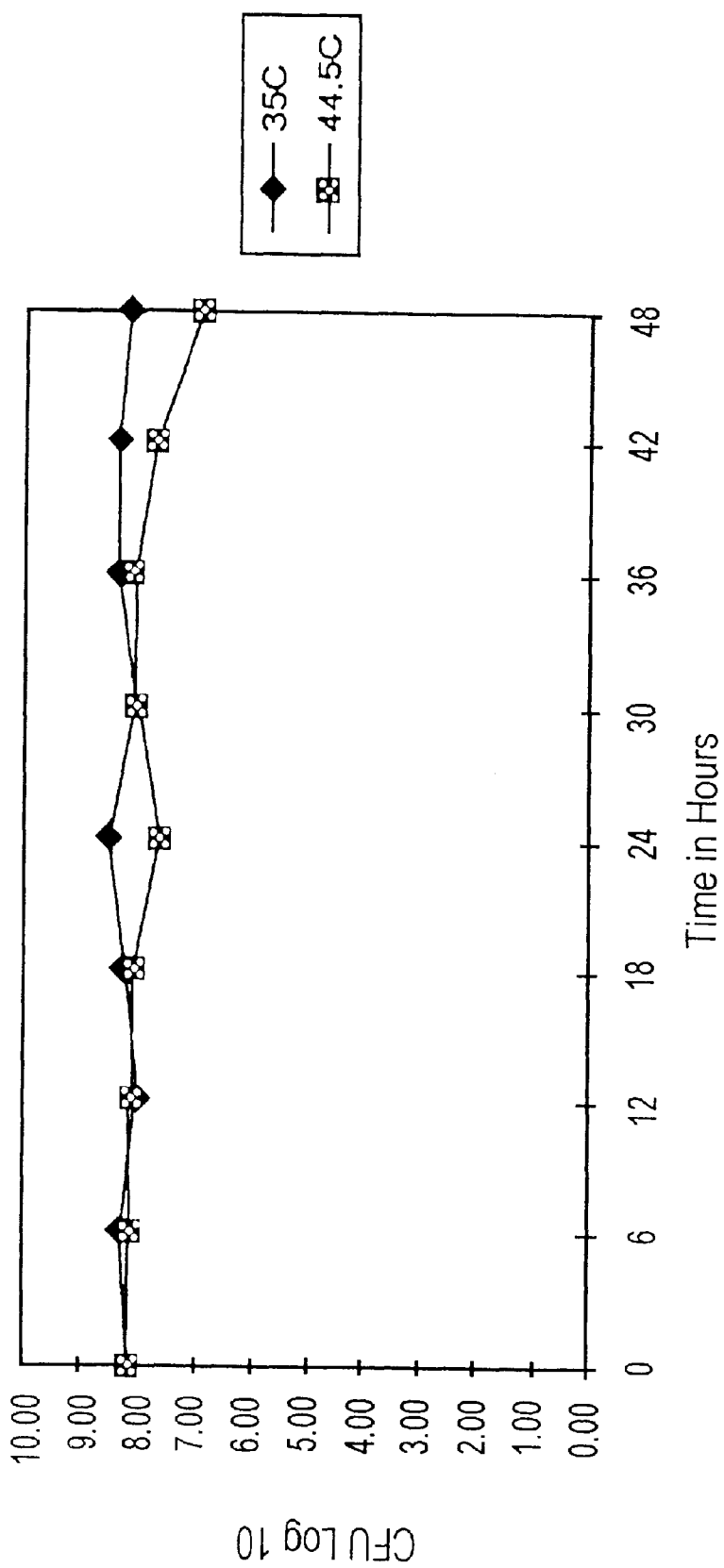
FIG. 7 is a line graph of an accelerated shelf-life study showing the viability over time of *Lactobacillus crispatus* CTV-05 preserved in a preservation matrix of the present invention which was fluid bed dried on maltodextrin.

FIG. 7 and Table 8 present data from a study in which a cell/preservation matrix suspension as described in Example 8 above was preserved on maltodextrin in a fluid bed dryer and then subjected to accelerated time storage conditions. For these studies, stability of product is defined as CFU values which meet product release criteria. Acceptable values were from $10^6$ to $10^8$ per suppository. These data show that the preservation matrix of the present invention had no loss of viability during 48 hours of storage at 35° C. The product which was stored at 44.5° C. remained stable for 18 hours. Between 18 and 24 hours, the viability dropped one log, but remained at approximately the same level for 42 hours. An additional log of viability was lost by 48 hours.

Figure 8:
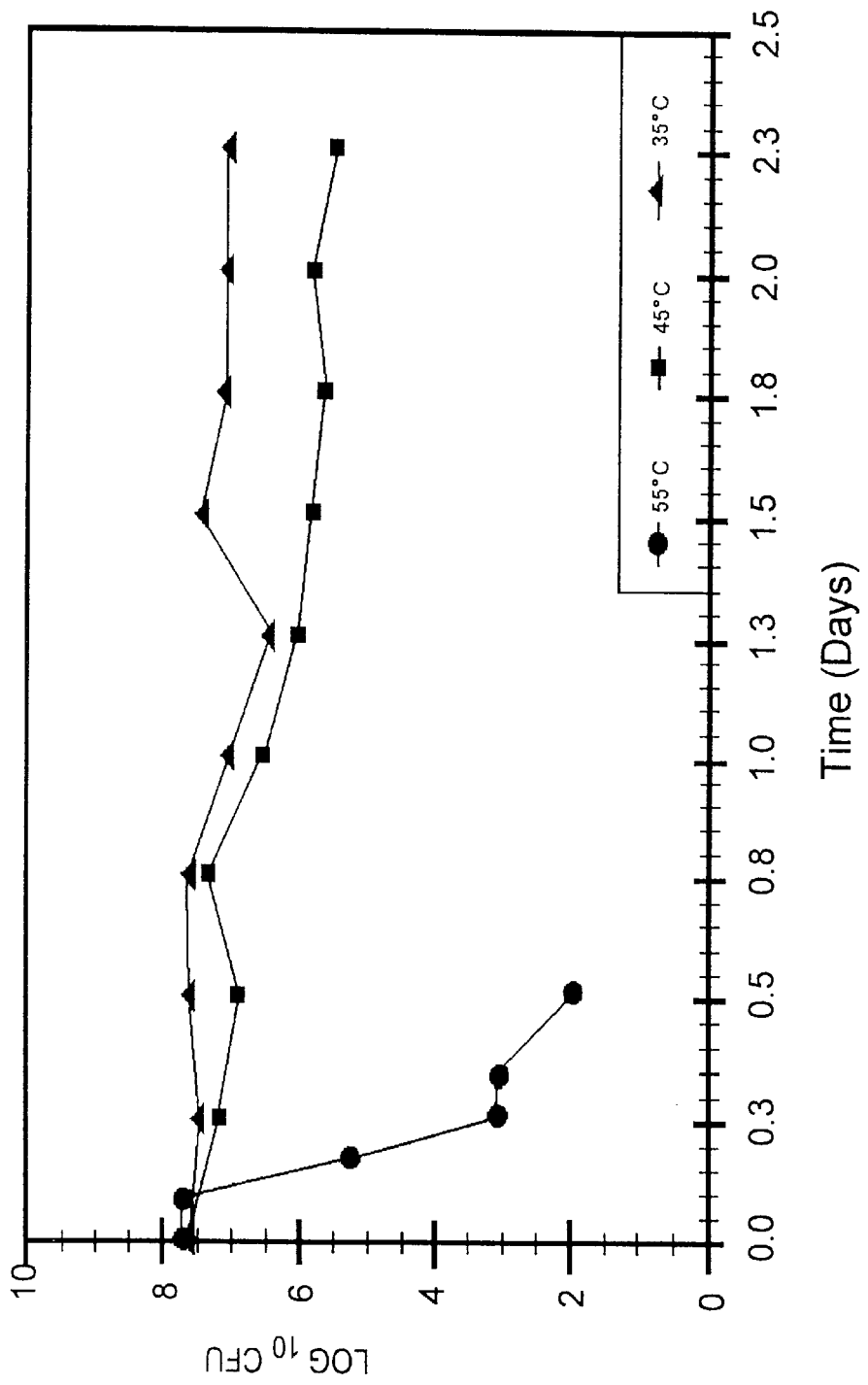
FIG. 8 is a line graph of an accelerated shelf-life study showing the viability over time of *Lactobacillus crispatus* CTV-05 preserved in a suspension matrix of the present invention.

These data correlate well with the accelerated and real time data from another accelerated shelf-life study in which the CTV-05 strain was preserved in the preservation matrix of the present invention by air drying. Table 9 shows that the CFU values of products which were stored refrigerated (2–8° C.) were stable at $10^8$ CFU for 25 months. The CFU values of products which were stored at room temperature (25° C. +5° C.) dropped from $10^8$ CFU to $10^7$ CFU at 2 months, but remained stable at $10^7$ CFU for 25 months. FIG. 8 shows results for the same product in an accelerated shelf-life study at 35° C., 45° C., and 55° C. At 35° C., the product lost less than 1 log of viability over about 2.3 days. At 45° C., the product lost about 2 logs of viability over about 2.3 days. At 55° C., the product lost viability rapidly within 0.5 days. A comparison of these accelerated time studies to the real time shelf-life studies demonstrates that it is reasonable to postulate that a product which is stable for 48 hours at 35° C. will remain stable for 25 months when stored at 2–8° C. or at room temperature.

TABLE 9

| | CFUs per Suppository | |
|---|---|---|
| Sample Age | Room Temperature (25° C. ± 5° C.) | Refrigerated (2–8° C.) |
| 1 week | 3.80E + 08 | Not Done |
| 2 weeks | 3.20E + 08 | Not Done |
| 3 weeks | 3.05E + 08 | Not Done |
| 1 month | 1.30E + 08 | 5.20E + 08 |
| 2 months | 9.80E + 07 | 2.20E + 08 |
| 3 months | 1.83E + 07 | 2.30E + 08 |
| 4 months | 3.25E + 07 | Not Done |
| 5 months | 3.80E + 07 | 2.80E + 08 |
| 6 months | 1.70E + 07 | 1.70E + 08 |
| 7 months | 1.60E + 07 | 2.60E + 08 |
| 9 months | 4.70E + 07 | 3.10E + 08 |
| 11 months | 2.80E + 07 | 2.50E + 08 |
| 15 months | 2.20E + 06 | 9.20E + 07 |
| 18 months | 4.70E + 06 | 1.50E + 07 |
| 25 months | 1.60E + 07 | 5.00E + 08 |

Example 10

The following example illustrates the use of cell wall fatty acid analysis to specifically identify suppository strains of Lactobacillus from a large sample of different Lactobacillus strains.

In this experiment, 242 Lactobacilli strains obtained from the vagina were evaluated in a blinded manner. The whole cell walls of bacteria were extracted by standard methods in the art. The cell wall fatty acid methyl esters were then analyzed by gas chromatography. A MIDI computer program then searched for "best fit" of the cell fatty acid profile with the known cell wall fatty acid profile of the known suppository strains. This computer program has a customized library of vaginal strains, which was generated by the present inventors.

Of the 242 Lactobacillus strains analyzed, 19 of 19 suppository strains of *Lactobacillus crispatus* were correctly identified (i.e., the analysis had a sensitivity of 100%) (data not shown). In addition, 40 isolates were identified as being suppository-like (i.e., the analysis had a specificity of 82%) (data not shown). Therefore, the cell wall fatty acid analysis is an effective, highly sensitive and specific method for identifying and tracking the suppository strains, even within a large sample number of Lactobacillus strains.

Example 11

The following example demonstrates the inhibitory effect of *Lactobacillus crispatus* CTV-05 on clinical isolates of *Candida albicans,* whereas other Lactobacillus isolates did not exhibit the inhibitory effect.

MRS agar was allowed to harden at a 5 mm slant. *Lactobacillus crispatus* CTV-05 was streaked across the diameter of the plate and was grown for 24, 48 or 72 hours under both anaerobic and ambient atmospheres. Control strains of *Lactobacillus jensenii* CTV-01, *Lactobacillus crispatus* CTV-02, *Lactobacillus crispatus* CTV-03, and *Lactobacillus crispatus* CTV-04 were grown in the same way. The plates were overlayed with YM agar with 10 mM CNNaS (sodium thiocyanate, previously reported to be an inhibitor of yeast growth) or without CNNaS. The agar overlays were inoculated with one of two strains of *Candida albicans* ATCC 60193 (cervical isolate) or *Candida albicans* ATCC 14053 (human blood isolate). Zones of inhibition were measured. *Lactobacillus crispatus* CTV-05 cells grown under ambient atmosphere were weak and unable to inhibit either Candida strain with or without CNNaS. In contrast, *Lactobacillus crispatus* CTV-05 cells grown anaerobically for 24, 48 or 72 hours effectively inhibited growth of both Candida strains. The addition of CNNaS to the medium did not increase the efficiency of inhibition. Therefore, *Lactobacillus crispatus* CTV-05 inhibits yeast growth in vitro. Table 10 shows the results of five hydrogen peroxide producing clinical Lactobacillus isolates tested for their ability to inhibit the growth of the *C. albicans* ATCC 60193 cervical isolate. The results show that *Lactobacillus crispatus* CTV-05, which has identifying characteristics of a Lactobacillus strain of the present invention, is clearly superior to any of the other isolates in inhibiting growth of the yeast organism.

TABLE 10

| Lactobacillus Organism | Organism Growth Time Period | Zone of Inhibition (in millimeters) |
| --- | --- | --- |
| Lactobacillus crispatus CTV-05 | 48 hours 72 hours | 70 to 0 mm 70 to 0 mm |
| Lactobacilllus jensenii CTV-01 | 48 hours | 1 to 0 mm |
| Lactobacillus crispatus CTV-02 | 48 hours | 3 to 0 mm |
| Lactobacillus crispatus CTV-03 | 48 hours | slight inhibition |

TABLE 10-continued

| Lactobacillus Organism | Organism Growth Time Period | Zone of Inhibition (in millimeters) |
| --- | --- | --- |
| Lactobacillus crispatus CTV-04 | 48 hours | 5 to 2 mm |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed:

1. A vaginal medicant, comprising:
    a bacterial culture of an isolated strain of the genus *Lactobacillus* having identifying characteristics comprising:
        (i) a percent vaginal epithelial cell (VEC) cohesion value of greater than 50%; and
        (ii) an ability to produce greater than 0.5 ppm of $H_2O_2$ under effective culture conditions.

2. The vaginal medicant of claim 1, wherein said strain has an ability to produce greater than 10 ppm of $H_2O_2$ under effective culture conditions.

3. The vaginal medicant of claim 1, wherein said strain sustains colonization of vaginal epithelial cells in vivo for greater than 1 month.

4. The vaginal medicant of claim 1, wherein said strain adheres to vaginal epithelial cells when said strain is in a metabolically inactive state.

5. The vaginal medicant of claim 1, wherein a single cell of said strain is from about 1 micron to about 2 microns in width and from about 2 microns to about 4 microns in length.

6. The vaginal medicant of claim 1, wherein said strain produces greater than 0.75 mg/100 ml of lactic acid under effective culture conditions.

7. The vaginal medicant of claim 1, wherein said matrix maintains greater than $10^7$ viable cells for a period of greater than 12 months in vitro.

8. The vaginal medicant of claim 1, wherein said matrix maintains greater than $10^6$ viable cells for a period of greater than 12 months at a temperature from about 4° C. to about 6° C. in vitro.

9. The vaginal medicant of claim 1, wherein said matrix maintains greater than $10^6$ viable cells for a period of greater than 12 months at about room temperature in vitro.

10. The vaginal medicant of claim 1, wherein said matrix has a pH of from about 5.0 to about 7.0.

11. The vaginal medicant of claim 1, wherein said strain is *Lactobacillus crispatus*.

12. The vaginal medicant of claim 1, wherein said strain is *Lactobacillus jensenii*.

13. A method to reduce the risk of infection in a female from a vaginal infection, comprising administering to a female a vaginal medicant comprising a bacterial culture of an isolated strain of the genus Lactobacillus having identifying characteristics comprising:
    (i) percent vaginal epithelial cell (VEC) cohesion value of greater than 50%; and
    (ii) an ability to produce greater than 0.5 ppm of $H_2O_2$ under effective culture conditions.

14. The method of claim 13, wherein said vaginal infection is an infection selected from the group consisting of bacterial vaginosis, symptomatic yeast vaginitis, gonorrhea, chlamydia, trichomoniasis, human immunodeficiency virus infection, urinary tract infection and pelvic inflammatory disease.

15. A method to treat a vaginal infection, comprising administering to a female having a vaginal infection a vaginal medicant comprising a bacterial culture of an isolated strain of the genus Lactobacillus having identifying characteristics comprising:
  (i) a percent vaginal epithelial cell (VEC) cohesion value of greater than 50%; and
  (ii) an ability to produce greater than 0.5 ppm of $H_2O_2$ under effective culture conditions.

16. A method to reduce the risk of infection of a human by human immunodeficiency virus (HIV), comprising administering to a human a medicant comprising a bacterial culture of an isolated strain of the genus Lactobacillus having identifying characteristics comprising:
  (i) a percent vaginal epithelial cell (VEC) cohesion value of greater than 50%; and
  (ii) an ability to produce greater than 0.5 ppm of $H_2O_2$ under effective culture conditions.

17. The method of claim 16, wherein administration of said medicant reduces the risk of HIV infection of said human by greater than two-fold.

18. A method to prevent infection of a human by symptomatic yeast vaginitis, comprising administering to a human a medicant comprising a bacterial culture of an isolated strain of the genus Lactobacillus having identifying characteristics comprising:
  (i) a percent vaginal epithelial cell (VEC) cohesion value of greater than 50%; and
  (ii) an ability to produce greater than 0.5 ppm of $H_2O_2$ under effective culture conditions.

19. The method of claim 18, wherein said strain is *Lactobacillus crispatus CTV-05*.

20. A method to reduce the risk of infection of a human by a gastrointestinal infection, comprising administering to a human a medicant comprising a bacterial culture of an isolated strain of the genus *Lactobacillus* having identifying characteristics comprising:
  (i) a percent vaginal epithelial cell (VEC) cohesion value of greater than 50%; and
  (ii) an ability to produce greater than 0.5 ppm of $H_2O_2$ under effective culture conditions.

21. A method to reduce the occurrence of preterm birth, comprising administering to a pregnant female a medicant comprising a bacterial culture of an isolated strain of the genus Lactobacillus having identifying characteristics comprising:
  (i) a percent vaginal epithelial cell (VEC) cohesion value of greater than 50%; and
  (ii) an ability to produce greater than 0.5 ppm of $H_2O_2$ under effective culture conditions.

22. A method to enhance metabolism of estrogen in the vagina and bowel, comprising administering to a female a vaginal medicant comprising a bacterial culture of an isolated strain of the genus Lactobacillus having identifying characteristics comprising:
  (i) a percent vaginal epithelial cell (VEC) cohesion value of greater than 50%; and
  (ii) an ability to produce greater than 0.5 ppm of $H_2O_2$ under effective culture conditions.

23. A gastrointestinal medicant, comprising a bacterial culture of an isolated strain of the genus Lactobacillus having identifying characteristics comprising:
  (i) a percent vaginal epithelial cell (VEC) cohesion value of greater than 50%; and
  (ii) an ability to produce greater than 0.5 ppm of $H_2O_2$ under effective culture conditions.

* * * * *